(12) United States Patent
Steen et al.

(10) Patent No.: US 9,084,416 B2
(45) Date of Patent: Jul. 21, 2015

(54) CONTAINER AND SUPPORTING STRUCTURE FOR HOUSING AN ORGAN

(75) Inventors: Stig Steen, Lund (SE); Audrius Paskevicius, Lund (SE); Anna Beyer, Lund (SE); Morgan Johansson, Lerberget (SE); Benjamin King, Takaka (NZ); Anna Soderlund, Gavle (SE); Anders Lindsten, Lund (SE); Peter Sebelius, Malmo (SE); Maria Sperlingsson, Lund (SE); Joakim Nilsson, Hoor (SE)

(73) Assignee: VIVOLINE MEDICAL AB, Lund (SE)

( * ) Notice: Subject to any disclaimer, the term of this patent is extended or adjusted under 35 U.S.C. 154(b) by 193 days.

(21) Appl. No.: 13/498,160

(22) PCT Filed: Sep. 24, 2010

(86) PCT No.: PCT/SE2010/000232
§ 371 (c)(1),
(2), (4) Date: Mar. 26, 2012

(87) PCT Pub. No.: WO2011/037512
PCT Pub. Date: Mar. 31, 2011

(65) Prior Publication Data
US 2012/0184024 A1    Jul. 19, 2012

Related U.S. Application Data

(60) Provisional application No. 61/278,459, filed on Oct. 8, 2009.

(30) Foreign Application Priority Data

Sep. 25, 2009 (SE) .................................... 0901242
Nov. 6, 2009 (SE) .................................... 0901422

(51) Int. Cl.
*A01N 1/00* (2006.01)
*A01N 1/02* (2006.01)
*C12M 3/00* (2006.01)
*C12M 1/36* (2006.01)
*C12M 1/38* (2006.01)

(52) U.S. Cl.
CPC ............ *A01N 1/0247* (2013.01); *A01N 1/0273* (2013.01)

(58) Field of Classification Search
USPC ............................................ 435/283.1–309.4
See application file for complete search history.

(56) References Cited

U.S. PATENT DOCUMENTS

| | | | |
|---|---|---|---|
| 5,586,438 A | 12/1996 | Fahy | |
| 5,807,737 A * | 9/1998 | Schill et al. | ................ 435/284.1 |
| 6,046,046 A | 4/2000 | Hassancin | |

(Continued)

FOREIGN PATENT DOCUMENTS

| | | |
|---|---|---|
| DE | 10121159 | 11/2002 |
| WO | 2007124044 | 11/2007 |
| WO | 2009136838 | 11/2009 |

OTHER PUBLICATIONS

International Search Report for PCT/ SE2010/000232, Completed by the Swedish Patent Office on Dec. 20, 2010, 3 Pages.

*Primary Examiner* — Nathan Bowers
*Assistant Examiner* — Lydia Edwards
(74) *Attorney, Agent, or Firm* — Birch, Stewart, Kolasch & Birch, LLP

(57) ABSTRACT

An apparatus intended for evaluation, preservation and perfusion of an organ, such as a lung. The apparatus includes a container with a bottom portion, an insert portion and a lid portion. A pulmonary artery tube is intended to be connected to the lung pulmonary artery and a trachea tube is intended to be connected to the trachea of the lungs and bent tube connects the pulmonary artery tube to a circuit for providing a fluid to the pulmonary artery is provided. The circuit includes a pump, an oxygenator, an optional leukocyte-filter, and a holder for connecting the trachea tube to a source of respiration. There is an oxygenator tube set and a leukocyte-filter tube set. A supporting structure for the container comprises a recess sized for enclosing said container and a display panel. Moreover, there are two handles, which may be unfolded into a position for supporting a sterile cloth.

8 Claims, 26 Drawing Sheets

(56) References Cited

U.S. PATENT DOCUMENTS

| | | |
|---|---|---|
| 2005/0147958 A1 * | 7/2005 | Hassanein et al. ............ 435/1.1 |
| 2008/0017194 A1 * | 1/2008 | Hassanein et al. ....... 128/200.24 |
| 2008/0208351 A1 | 8/2008 | Besenbacher et al. |
| 2009/0197241 A1 | 8/2009 | Fishman et al. |
| 2011/0065169 A1 | 3/2011 | Steen et al. |
| 2011/0136096 A1 | 6/2011 | Hassanein et al. |

* cited by examiner

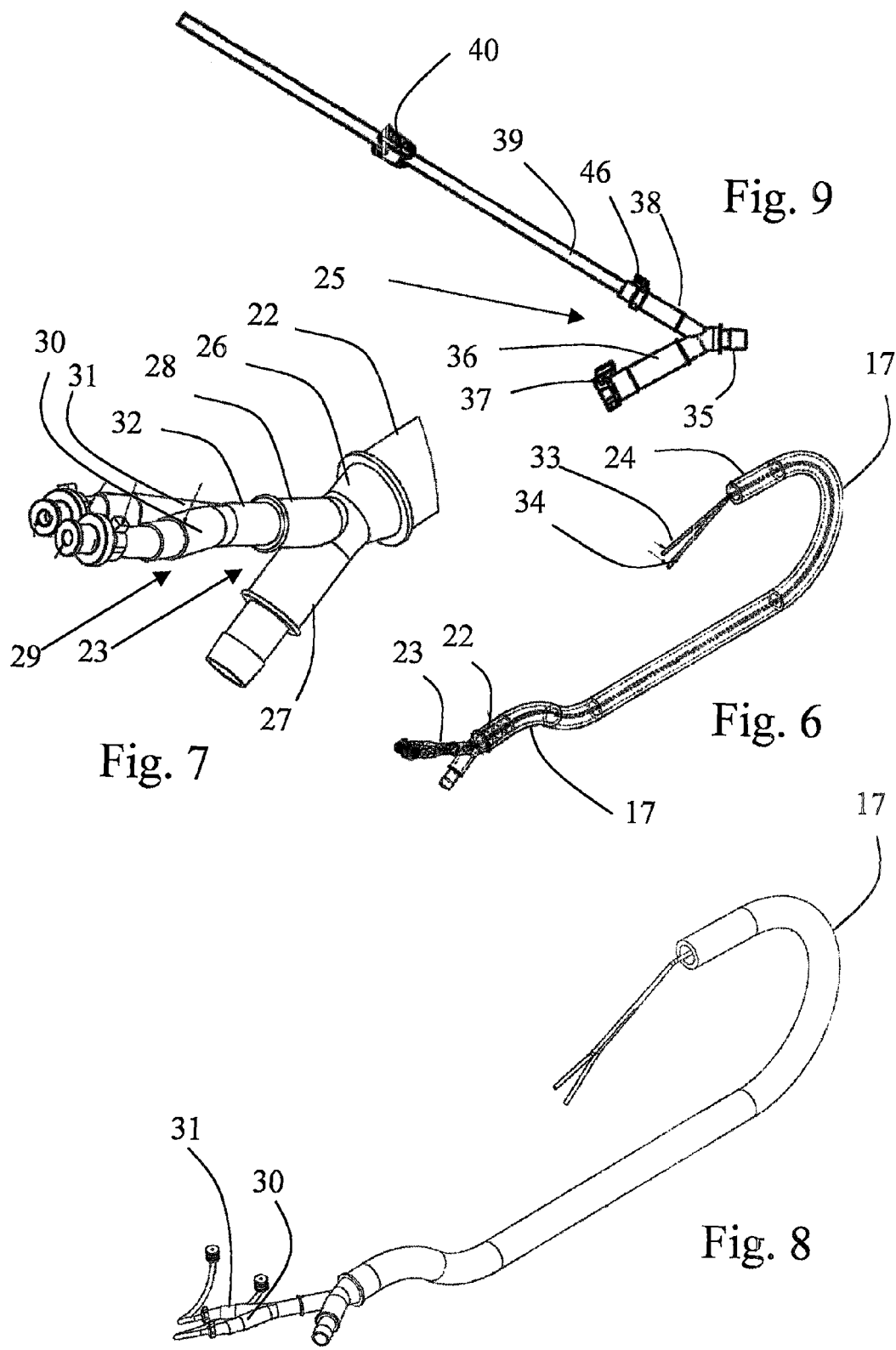

CONTAINER AND SUPPORTING STRUCTURE FOR HOUSING AN ORGAN

CROSS-REFERENCE TO RELATED APPLICATION

This application is the U.S. national phase of PCT Appln. No. PCT/SE2010/000232 filed Sep. 24, 2010, which claims priority to Swedish application 0901242.8 filed on Sep. 25, 2009; Swedish application 0901422.6 filed on Nov. 6, 2009, and also claims the benefit of U.S. provisional application 61/278,459, filed on Oct. 8, 2009, the disclosures of which are incorporated in their entirety by reference herein.

FIELD OF INVENTION

The present invention relates to a container comprising several tube sets and a supporting structure therefore.

BACKGROUND OF THE INVENTION

Patent publication WO 2009/136838A1 discloses an apparatus for housing an organ during evaluation and preservation. The organ may be the lungs. The embodiments and drawings discloses a container which is suitable for evaluation and preservation of the lungs. The apparatus is shown without any details as to the disposable products for connection of the organ. Thus, there is a need for connectors, tubes, sensors, and other devices making the above-mentioned apparatus more versatile.

SUMMARY OF THE INVENTION

Accordingly, an object of the present invention is to mitigate, alleviate or eliminate one or more of the above-identified deficiencies and disadvantages singly or in any combination.

According to a first aspect, there is provided a container intended for evaluation, preservation and/or perfusion of an organ, consisting of a lung, comprising: a bottom portion, an insert portion and a lid portion; a pulmonary artery tube intended to be connected to the lung pulmonary artery: a trachea tube intended to be connected to the trachea of the lungs; a bent tube for connection of the pulmonary artery tube to a circuit for providing a fluid to the pulmonary artery, said circuit comprising a pump and an oxygenator and an optional leukocyte-filter, said bent tube being bent over about 180 degrees; a holder for connecting the trachea tube to a source of ventilation, wherein said trachea tube and said bent tube are arranged to pass through one and the same side wall of the container.

In an embodiment, the container may further comprise a tube set arranged outside of the container for enclosing fluid to be circulated through the organ, said tube set being arranged as a cassette. The container may further comprise an oxygenator tube set and optionally a leukocyte-filter tube set. In addition, the container may comprise a vortex preventing plate.

In a further embodiment, the container may further comprise a topical cooling cloth provided with a pocket and a narrow tube extending into said pocket for providing cold fluid to said pocket and to said cloth.

In another embodiment, the container may further comprise pressure sensor tubes and temperature measurement sensors, having lead-through arrangements passing through one and the same side wall of the container as said trachea tube and said bent tube.

In another aspect, there is provided a supporting structure for a container as mentioned above comprising a recess sized for enclosing said container whereby an air space is formed between the container and the supporting structure. The structure may further comprise comprising handles which may be unfolded into a position for supporting a sterile cloth. Said sterile cloth may be arranged in a vertical plane and at the structure and across the container arranged at the structure, so that said side wall having the trachea tube and the bent tube passing therethrough is arranged at one side of said sterile cloth and forming a non-sterile area, while the other side of the sterile cloth forms a sterile area.

In a further embodiment, the supporting structure may comprise a priming tube set. In addition, the supporting structure may further comprise at least one of the following components: a water pump, a heating and cooling unit, a power supply, a battery pack, a loudspeaker, a pneumatics unit and a fluid pump unit.

BRIEF DESCRIPTION OF THE DRAWINGS

Further objects, features and advantages of the invention will become apparent from the following detailed description of embodiments of the invention with reference to the drawings, in which:

FIG. 6 is a perspective view of a bent tube.

FIG. 7 is an enlarged perspective view of an end portion of the bent tube of FIG. 6.

FIG. 8 is a perspective view of a second embodiment of the bent tube.

FIG. 9 is a plan view of a portion of the tube set.

DETAILED DESCRIPTION OF EMBODIMENTS

Below, several embodiments of the invention will be described. These embodiments are described in illustrating purpose in order to enable a skilled person to carry out the invention and to disclose the best mode. However, such embodiments do not limit the scope of the invention. Moreover, other combinations of the different features are possible within the scope of the invention.

Figure 1:
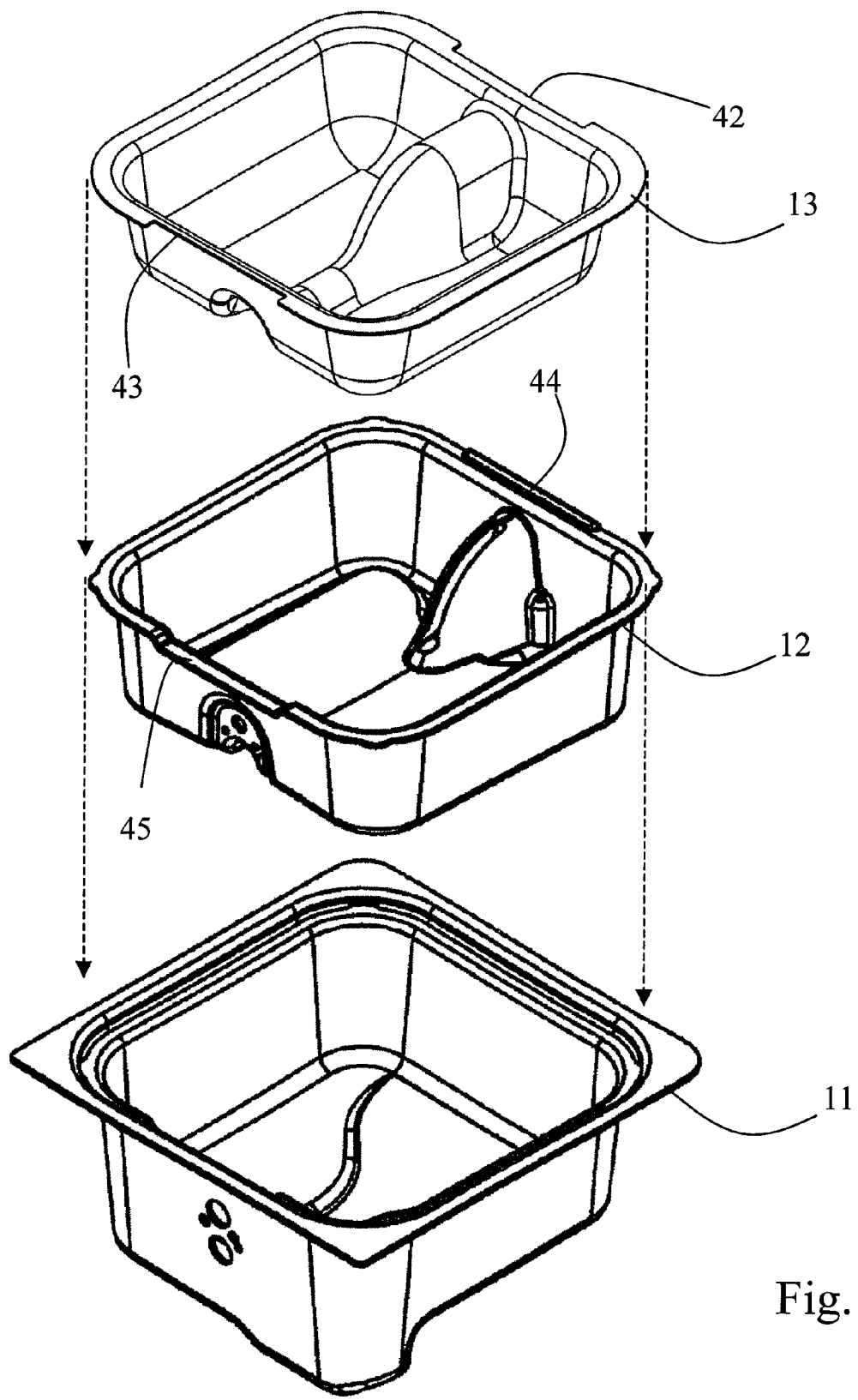
FIG. 1 is a perspective exploded view of a container intended for evaluation and preservation of an organ, such as lungs.

FIG. 1 shows an embodiment of a container intended for enclosing a lung-heart-block or lungs during evaluation and/or preservation. Evaluation may include conditioning of the lungs and other interventions such as treatment with penicillin or surgical interventions if required. The organ is described below to be lungs but other organs may be used, such as heart, liver, kidney, pancreas, intestines etc. The operation of the device is described in patent publication WO 2009/136838 A1, the contents of which is incorporated in the present specification by reference.

In a first embodiment, the container comprises three portions as shown in FIG. 1. A bottom portion 11 forms an enclosure. An insert portion 12 is intended to be arranged in the bottom portion 11 as shown by arrows. A lid portion 13 may be arranged at the bottom portion having the insert arranged therein.

Figure 33:
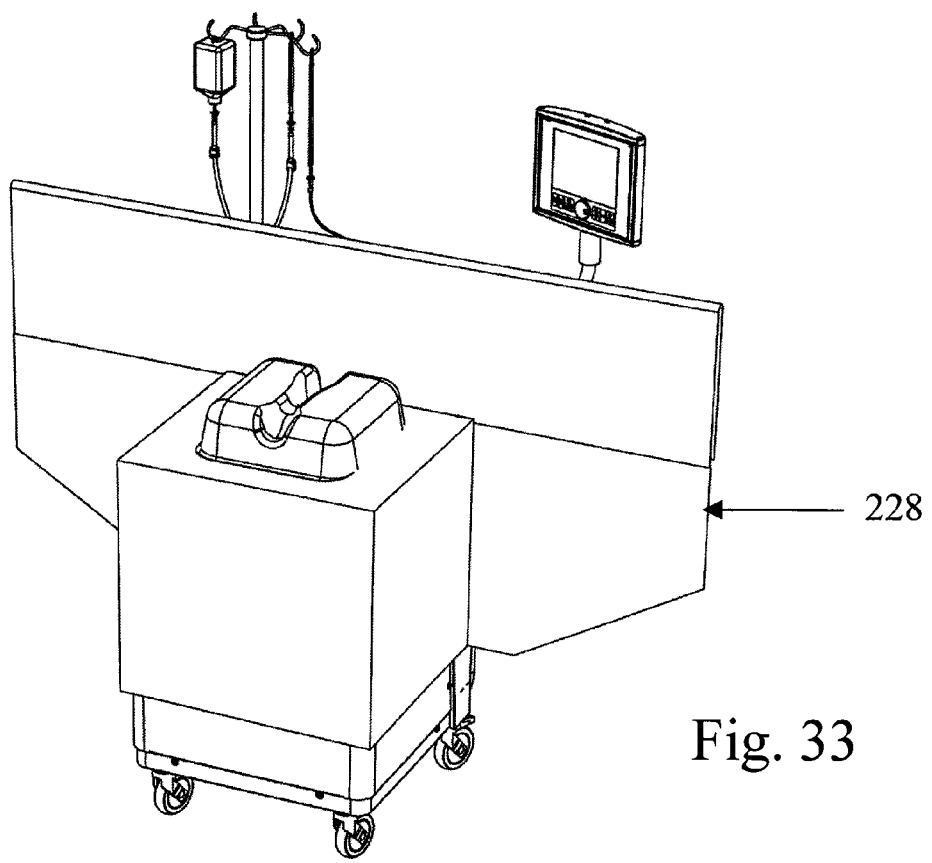

The lid portion 13 may be arranged in the shown position according to arrows, or in an inverted position, see for example FIG. 33. The lid portion is provided with two recesses 42 and 43 at opposite sides. There is a shoulder 44 at the insert portion 12, which mates with one of said recesses 42, 43. Thus, the lid may be placed in the shown position or rotated 180° around a vertical axis. The lid may also be rotated 180° around a vertical axis, so that the lid is inverted. Thus, the lid may occupy four different positions. A recess 45 in the insert ensures that the inner space of the container is always ventilated so that no.

Figure 2:
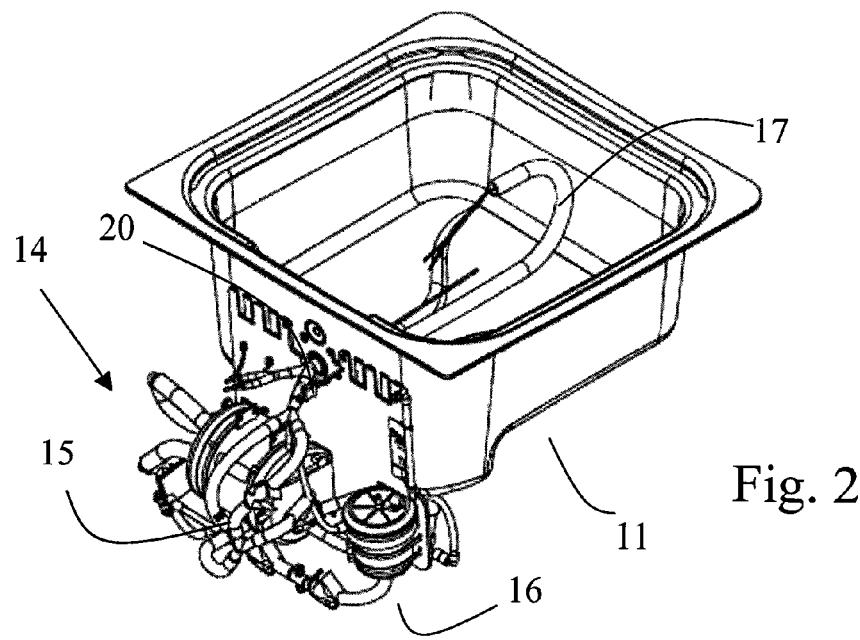
FIG. 2 is a perspective view of an embodiment of the bottom portion provided with tube sets.

FIG. 2 shows the bottom portion 11 provided with a tube set 14. The tube set includes an oxygenator 15 and a leucocyte-filter 16.

Figure 3:
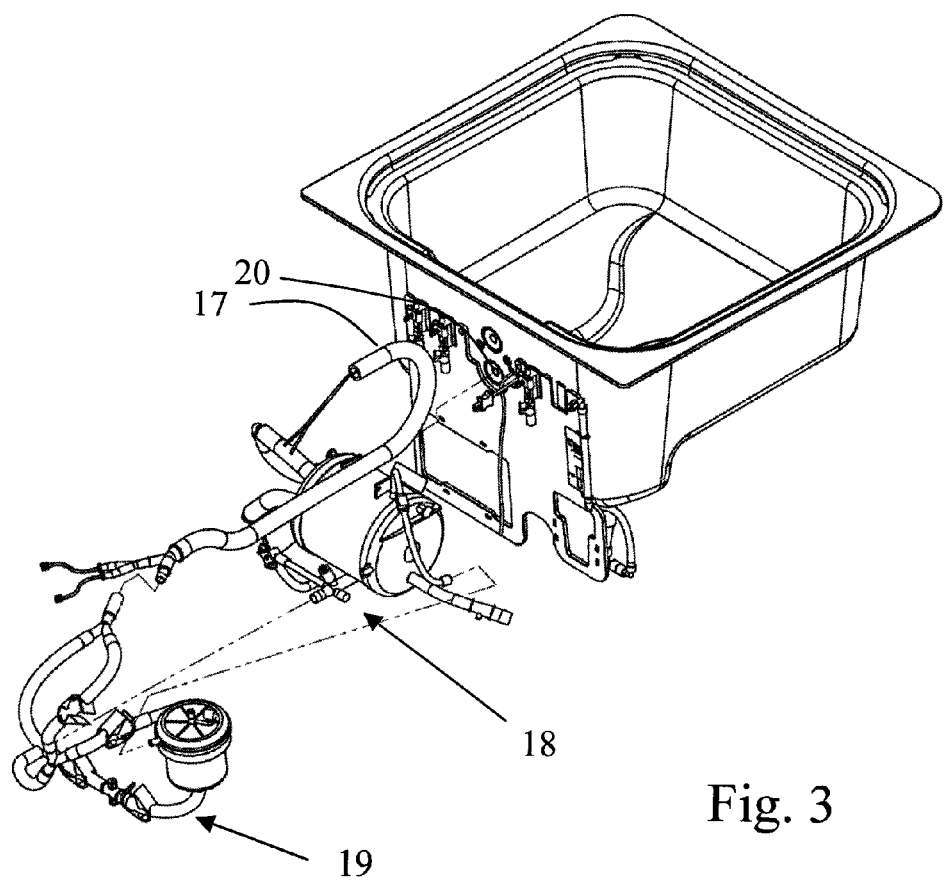
FIG. 3 is a perspective view of the embodiment of FIG. 2 with the tube set portions in an exploded view.

The tube set is shown in more detail in FIG. 3, which is en exploded view. The tube set comprises a bent tube 17, an oxygenator tube set 18 in connection with the oxygenator 15, shown in more detail in FIG. 13 and a leucocyte-filter tube set 19 shown in more detail in FIG. 12.

Figure 4:
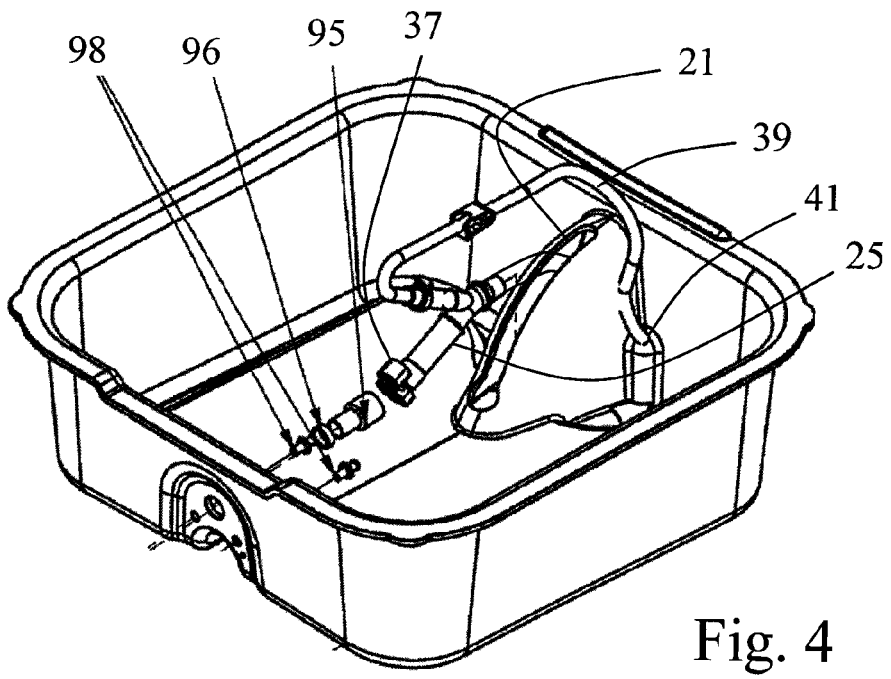
FIG. 4 is a perspective view of the embodiment of FIG. 2 showing the components inside the container.

The bent tube 17 is arranged through a hole 20 in the bottom portion 11 as shown in FIG. 3 and extends below the insert 12 and up through a slit 21 as shown in FIG. 4.

Figure 10:
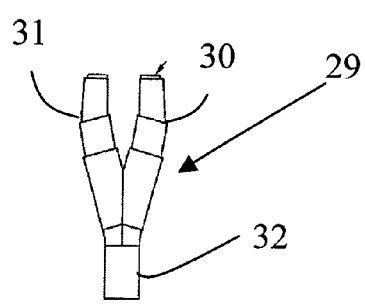
FIG. 10 is a plan view of another portion of the tube set.

The bent tube 17 is shown separately in FIG. 6. A first end 22 of the bent tube 17 is connected to a first Y-connector 23, which is shown in more detail in FIG. 7 and FIG. 10. A second end 24 of the bent tube 17 extends up through the slit 21 and is connected to a second Y-connector 25, which is shown in more detail in FIG. 9 and is also shown in FIG. 4.

Figure 15:
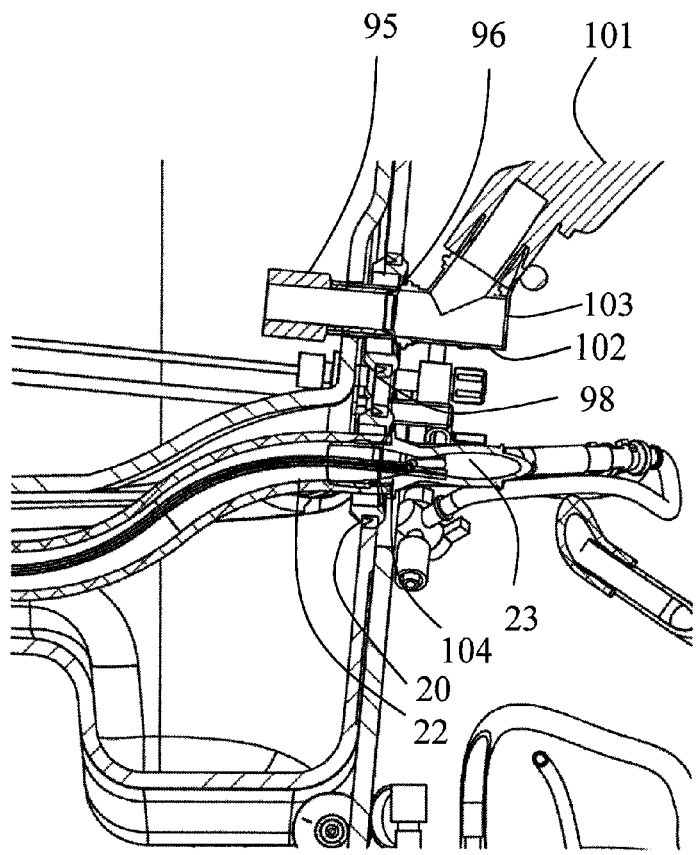
FIG. 15 is a partial cross-sectional view of a portion of the container according to the embodiment shown in FIG. 2.

As shown in FIG. 15, the hole 20 in the bottom portion 11 is provided with a sealing so that the bent tube 17 passes through the hole 20 and the sealing in a fluid tight manner. Thus, the first end 22 of the bent tube 17 extends through the hole 20 to the exterior of the bottom portion 11 as shown in FIG. 2.

As shown in more detail in FIG. 7, the first end 22 of bent tube 17 extending out through the hole 20 is provided with the first Y-connector 23, having a first connection leg 26, which is inserted in the first end 22 of the bent tube 17. A second connection leg 27 of the first Y-connector 23 is connected to the leucocyte-filter tube set 19, see FIG. 3. A third connection leg 28 of the first Y-connector 23 is connected to a third Y-connector 29, which is shown separately in detail in FIG. 10.

The third Y-connector comprises two soft legs 30 and 31 having decreasing cross-section and a connector leg 32, which is connected to the third connector leg 28 of the first Y-connector 23. Each of the two soft legs 30 and 31 comprises a narrow tube 33, 34, extending from said soft leg 30, 31 all the way through the third Y-connector 29, through the first Y-connector 23 and through the bent tube 17 to the second end 24 of the bent tube 17 and extending out through said second end 24 as shown in FIG. 2 and FIG. 6. At this extending end, each narrow tube comprises several holes adjacent the end, which extends out through the second end 24 of the bent tube 17. At the other end of the narrow tubes, at the soft legs 30, 31, each narrow tube 33, 34 ends in a Luer-connector. The narrow tubes are used for measuring the pressure at the extending end. The tubes may be used for other purposes, such as measuring other parameters, such as temperature or blood gases, or for introduction of substances or fluids.

An alternative design of the bent tube is shown in FIG. 8. The difference is that the Luer connectors at the end of the soft legs 30, 31 are replaced by fixed connections of flexible tubes for direct connection to pressure sensors. In addition, the soft legs 30, 31 are inclined in order to avoid trapping of air during priming.

The second end 24 of the bent tube 17 is connected to the second Y-connector 25 shown in more detail in FIG. 9. Thus, the extending ends of the narrow tubes 33, 34 extend inside the second Y-connector.

The second Y-connector 25 comprises a first leg 35 for connection with the second end 24 of the bent tube 17. A second leg 36 is at the end provided with a releasable coupling 37 as described in more detail below. A third leg 38 is connected to a tube 39 via a releasable coupling 46 and is provided with a clamp 40. The end of the tube 39 is inserted in a hole 41 in the insert 12 as shown in FIG. 4 and FIG. 5.

Figures 12, 13:
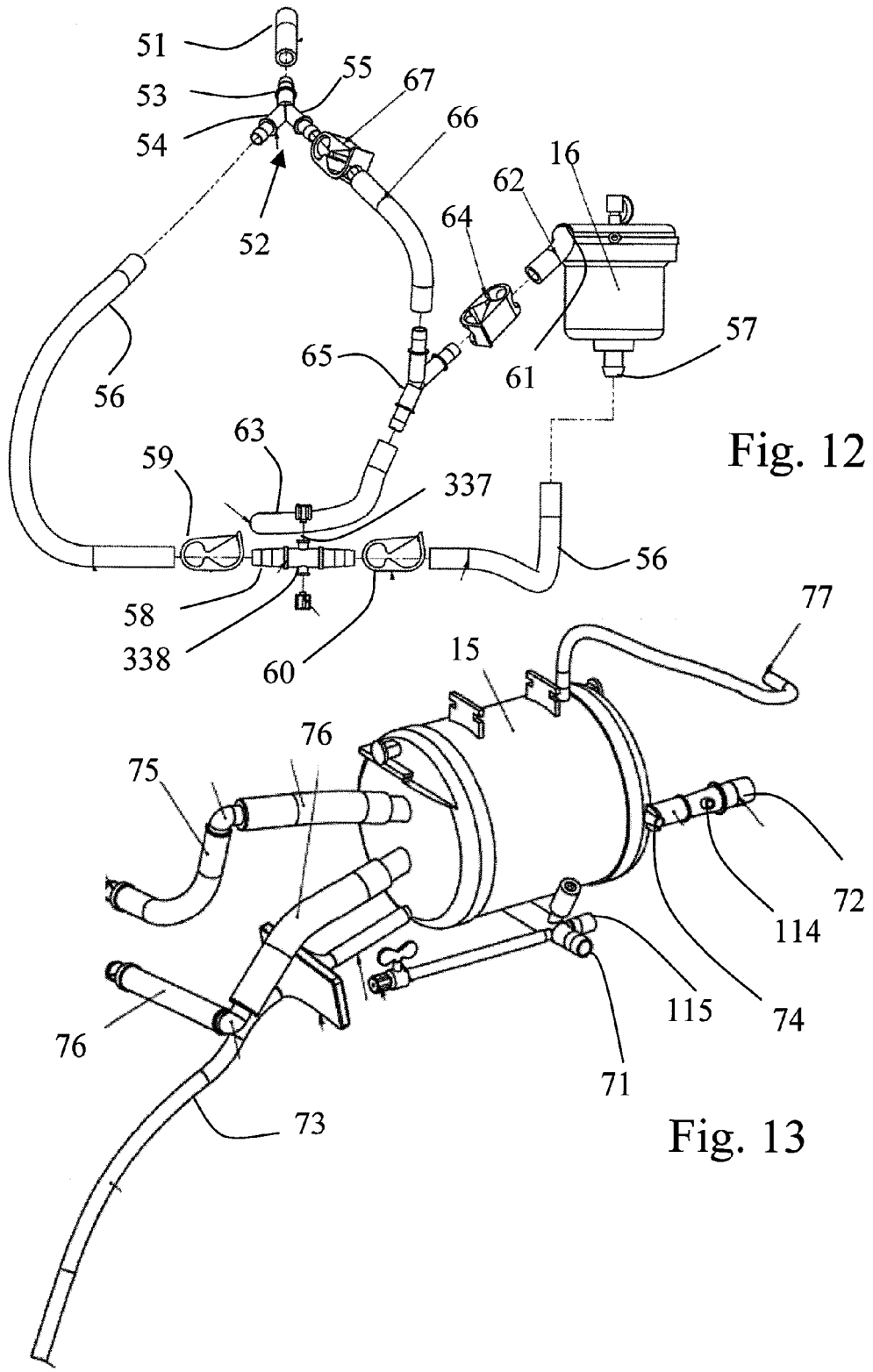
FIG. 12 is a partly exploded schematic view of a leukocyte filter tube set.
FIG. 13 is a partly exploded schematic view of an oxygenator tube set.

As shown in FIG. 3, the second connection leg 27 of the first Y-connector 23 is connected to the leucocyte-filter tube set 19 as further shown in FIG. 12.

Figure 5:
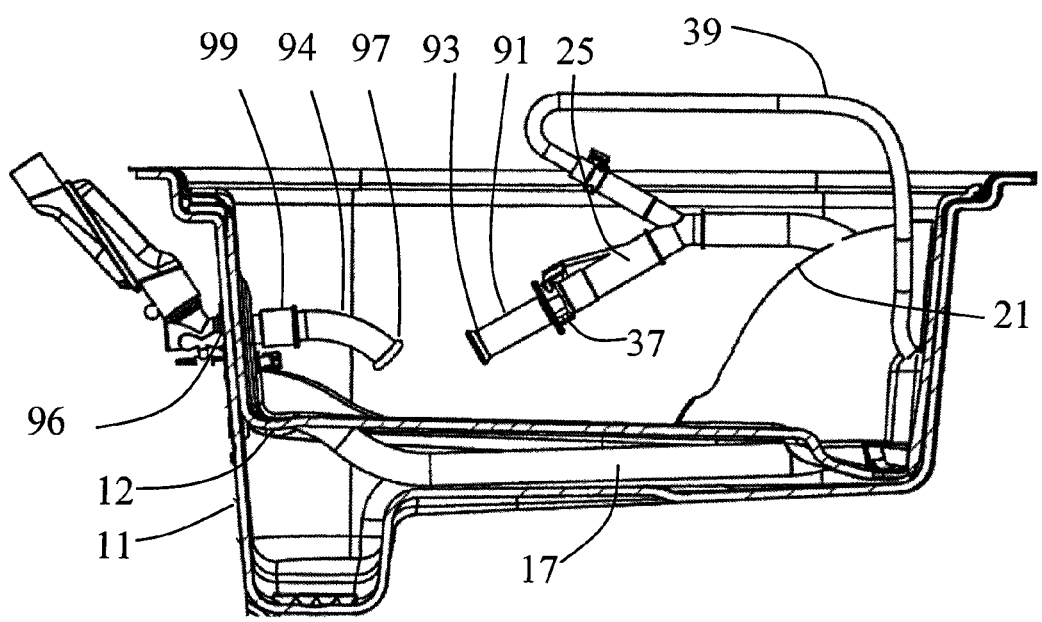
FIG. 5 is a cross-sectional view of the embodiment according to FIG. 2.

The container is shown in a cross-sectional view in FIG. 5. The bottom portion 11 is provided with the insert portion 12 and a space is formed between the portions. The bent tube 17 is arranged in said space and extends from in inlet portion to the left in FIG. 5, beneath the insert portion 12 and up through the slit 21. At the end of the bent tube, the second Y-connector 25 is arranged.

The Y-connector 25 ends with the releaseable coupling 37. A PA (pulmonary artery) tube 91 may be attached to the releasable coupling 37 via a mating coupling 92, see FIG. 11. The PA tube 91 is freely rotatable in the coupling. The other end of the PA tube 91 comprises a shoulder 93. The PA tube is intended to interact with the pulmonary artery of the lungs to be evaluated and/or preserved in order to introduce a fluid into the vascular system of the lungs 90, which are shown schematically in FIG. 11 as an oval body. Other types of organs may be connected in a similar manner. The fluid enters the lung vascular system via said PA tube 91 and exits the lungs directly to the surrounding space of the container and is collected at the bottom of the insert 12. Finally, the fluid passes to the space below the insert 12 and is circulated.

Figure 11:
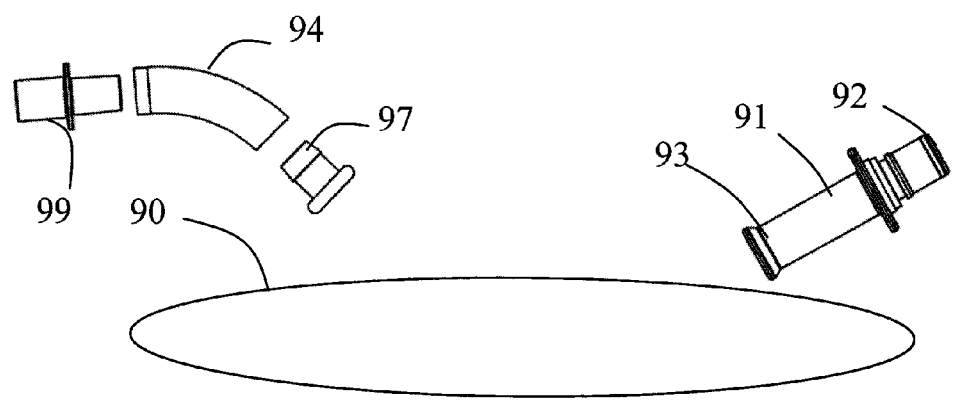
FIG. 11 is a plan view of a further portion of the tube set.

The trachea of the lungs 90 may be connected to a respiration system. For this purpose, a pulmonary connection set is arranged comprising a flexible tube 94. A connection shoulder portion 97 is arranged at the right side of the flexible tube, as seen in FIG. 5 and FIG. 11. The shoulder portion 97 may be inserted in the flexible tube and into a trachea of lungs to be evaluated and preserved in order to introduce and remove gas in the trachea and the lungs. At the left end of the flexible tube 94 as seen in FIG. 5 and FIG. 11, a connector 99 is arranged for connection to a lead-through tube 95, see FIG. 4, which is arranged at a side wall of the bottom portion 11 and insert portion 12 and leads through said portions. The lead-through tube 95 is sealed by a sealing 96 in relation to said portions. The tube 94 may be connected to other organs if desired.

By this arrangement, all connections through the side walls of the container are arranged at one and the same side surface of the container, which makes connection arrangement more easy. Furthermore, the container comprises a bottom outlet for fluid as described below. By this arrangement, sterility may not be compromised at the other sides.

Additional lead-through tubes 98 are arranged for passing pressure sensor tubings, see FIG. 4. The tubings may alternatively be used for taking samples from this location.

The length of the flexible tube 94 is adjustable by simply cutting it by a pair of scissors or a knife. Thus, the length of the flexible tube 94 may be adjusted to the lungs to be handled.

FIG. 12 shows the leucocyte filter tube set 19, which comprises a connector tube 51 for connection of said connection leg 27 to a first leg 53 of a Y-connector 52. A second leg 54 of the Y-connector is connected to a connection tube 56 for connection to a bottom connector 57 of a leucocyte-filter 16. Inserted in the connection tube 56 is a port portion 58 provided with two ports. The connection tube 56 also comprises two clamps 59 and 60. From the top of the leucocyte-filter 16 there is a connector 61, which is connected to a tube 62 extending to the oxygenator via end tube 63. The tube 62 comprises a clamp 64 and a Y-connector 65. A by-pass tube 66 is connected between the Y-connector 65 and a third leg 55 of the inlet Y-connector 52 and is provided with a clamp 67. Thus, by opening the clamp 67 and closing the clamp 64, the leucocyte-filter 16 may be by-passed, if the filter is not intended to be used. The filter may be replaced, for example if it has been clogged, by closing clamps 60 and 64.

End tube 63 is connected to an outlet connector 71 from the oxygenator 15, which is shown in FIG. 13. Fluid enters the oxygenator at an inlet connector 72 from a pump segment (not shown). Cooling water enters and exits the oxygenator at an inlet 75 and an outlet 76. The cooling water lines are insulated in order to avoid condensation. The oxygenator is provided with oxygen or air via inlet 73 and outlet 74. In addition, a venting tube 77 is arranged for removing possible air intrained inside the oxygenator.

Figure 14:
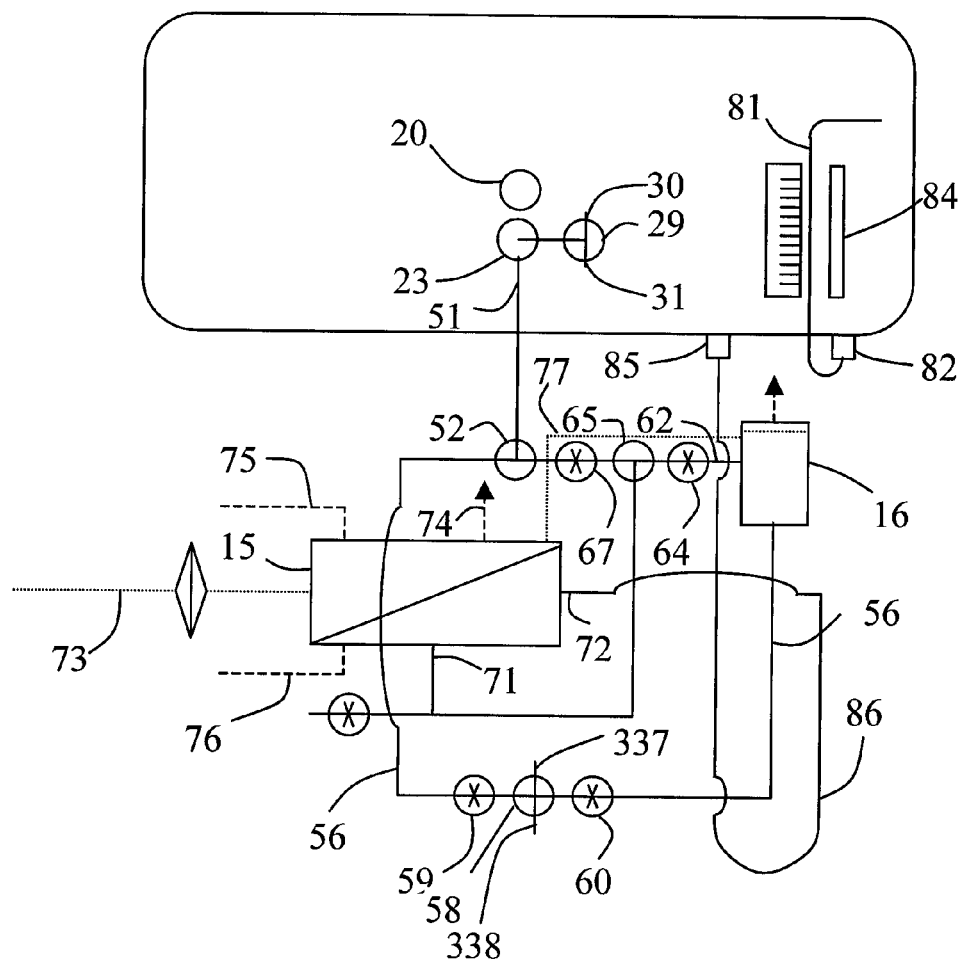
FIG. 14 is a schematic view of the tube sets according to FIGS. 12 and 13.

FIG. 14 shows the two tubing sets in a schematic manner. The same reference numbers has been used as in the previous figures.

FIG. 14 also shows a an ascension tube 81, which is connected to the bottom portion 11 at an outlet nipple 82. The ascension tube 81 extends outside the bottom portion and along a scale, which indicates the level of fluid inside the container and bottom portion. The fluid level is visible through the ascension tube 81, which is transparent. An monitoring level sensor may also be arranged to indicated the fluid level inside the container. An optical or capacity sensor may be arranged as shown by block 84.

A second outlet nipple 85 is arranged in the bottom portion. Nipple 85 is connected to a pump segment tube 86 which extends downwards to a peristaltic pump arranged as described below in connection with FIG. 34. The other end of the pump segment tube 86 is connected to the oxygenator inlet 72, see FIG. 13.

FIG. 15 is a cross-sectional view of the side walls of the bottom portion and insert portion showing a lead-through tube 95, which extends through the walls of said portions. The lead-through tube 95 is connected to an air filter 101 (only a portion of the filter is shown in FIG. 15), which is connected to a respiration apparatus (not shown). An inspection port 102 is normally closed by a lid 103, which is removeable for inspection and suction of the trachea.

Also visible in FIG. 15 is the end 22 of the bent tube 17 and the first Y-connector 23, which pass through the side wall of the bottom portion sealed by a sealing 104.

Figure 16:
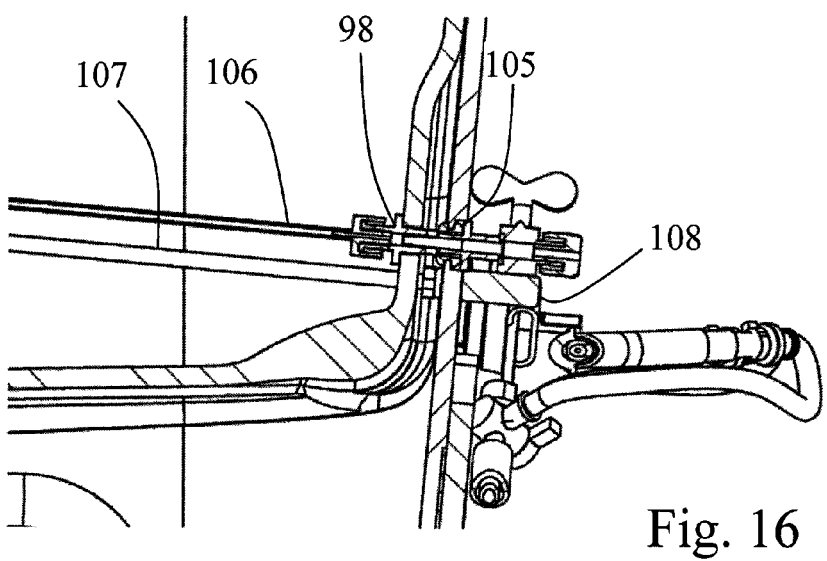
FIG. 16 is a partial cross-sectional view similar to FIG. 15 but in another plane.

The additional lead-through tubes 98 are shown in FIG. 16 and are sealed in relation to the bottom portion by sealings 105. A sampling tube 106 extends through the lead-through tube 98 so that a sample may be taken from any position inside the container via the flexible sampling tube 106. In addition, a temperature sensor 107 passes through another lead-through tube and ends in a contact 108 at the outside of the container. The contact is connected to a display as described below.

Figure 17:
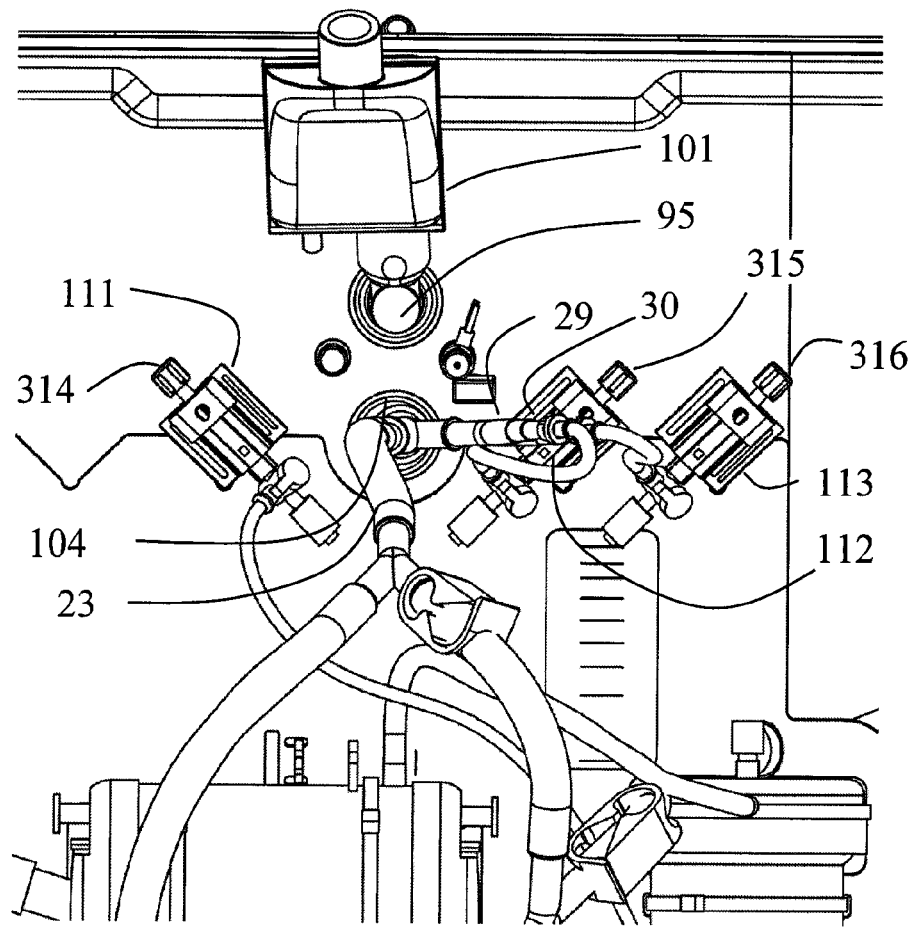
FIG. 17 is a partial side view of one of the walls of the container in the embodiment according to FIG. 2.

FIG. 17 shows a part of the bottom portion from an end view and shows the trachea lead-through tube 95 including the air filter 101. The first Y-connector 23 and the third Y-connector 29 extends from the sealing 104 including the two soft legs 30 and 31 (only one is visible in FIG. 17).

In addition, FIG. 17 shows three pressure sensors 111, 112, 113 arranged on the wall of the bottom portion. Two of the pressure sensors 112, 113 are connected to the Luer connectors at the end of the soft legs 30, 31 or directly to the narrow tubes. The third pressure sensor 111 is connected to a nipple 114 at the inlet of the oxygenator as shown in FIG. 13. Thus, the third pressure sensor 111 may monitor the pressure at the outlet of the pump and detect a fault condition in which an excessive pressure is built up in the tube system. If the pressure is too high, the pump is stopped.

Another temperature sensor 115 is arranged at the outlet of the oxygenator (see FIG. 13), in order to monitor the temperature of the fluid exiting the oxygenator and being delivered to the organ.

Figure 18:
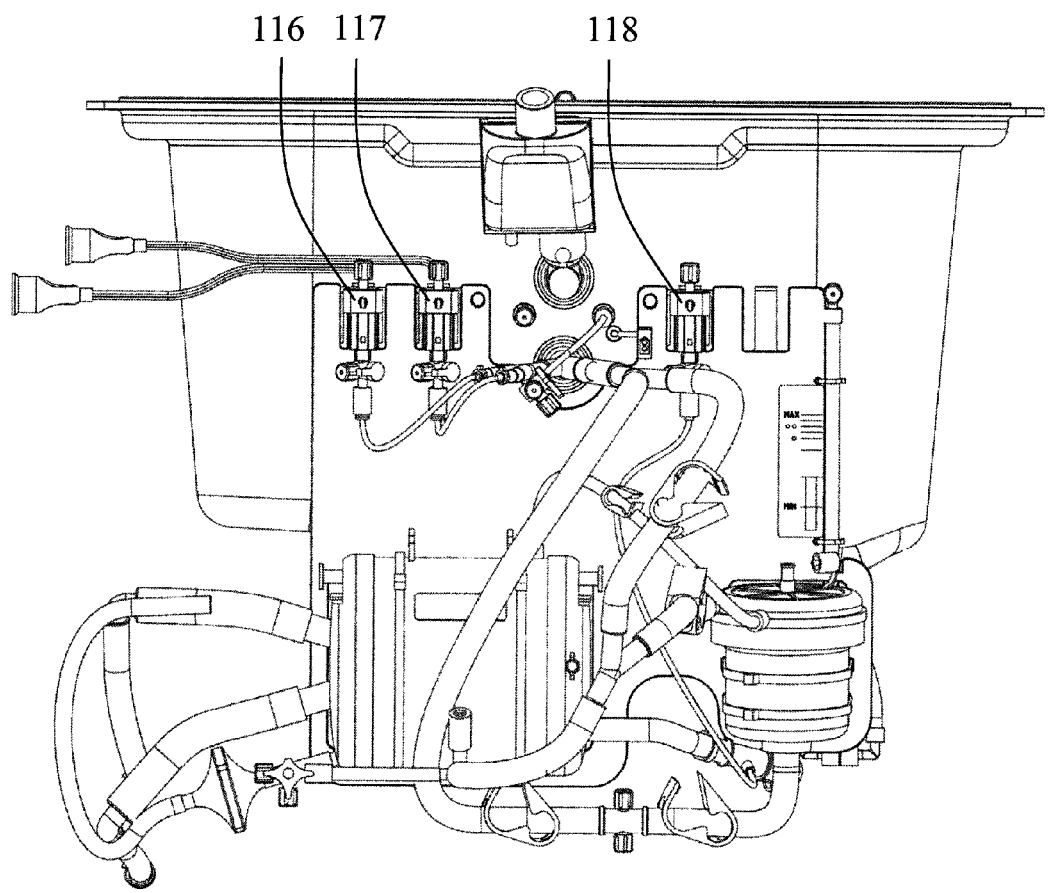
FIG. 18 is a side view of the container and tube sets according to another embodiment.
Figure 19:
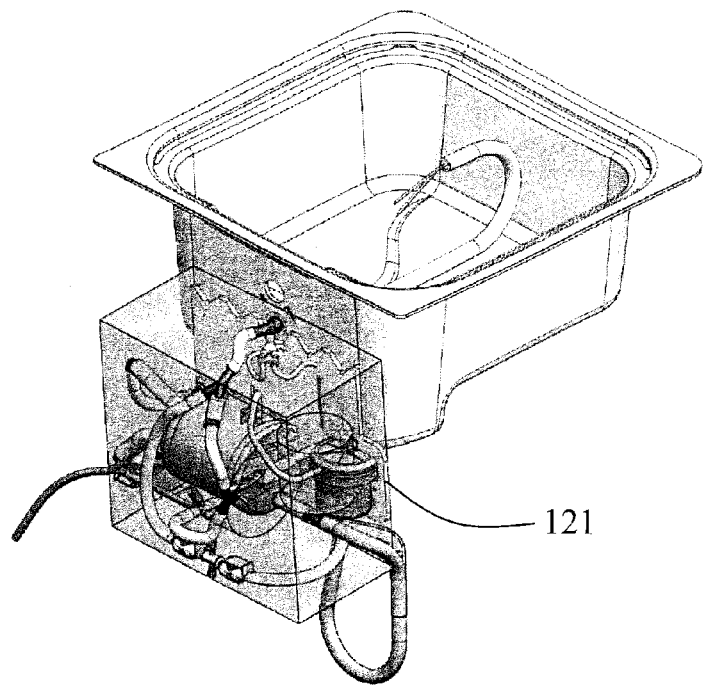
FIGS. 19 to 22 are perspective views of a first embodiment of a cassette for including the tube sets of the embodiment of the container according to FIG. 2.
Figure 20:
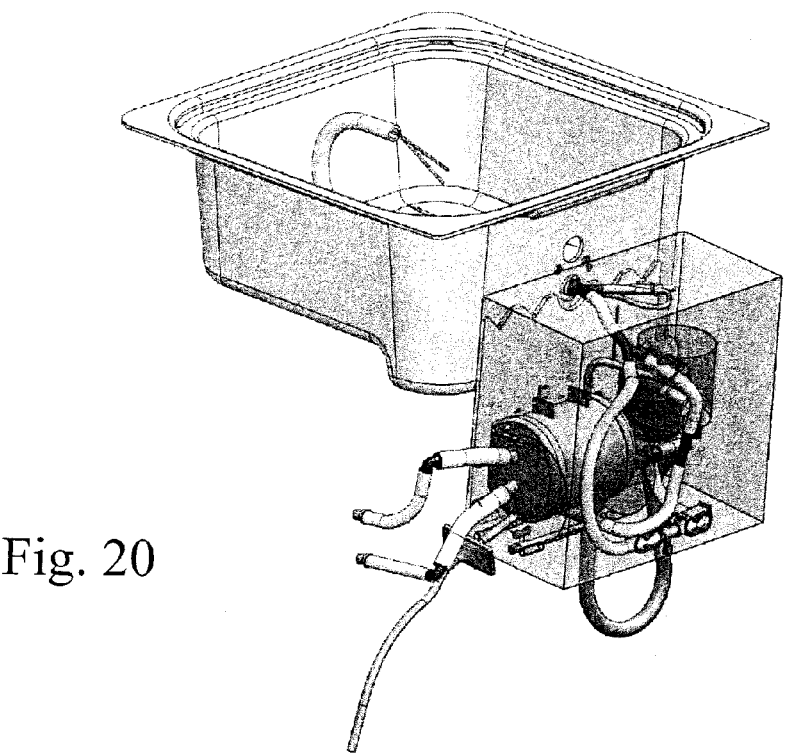
Figure 21:
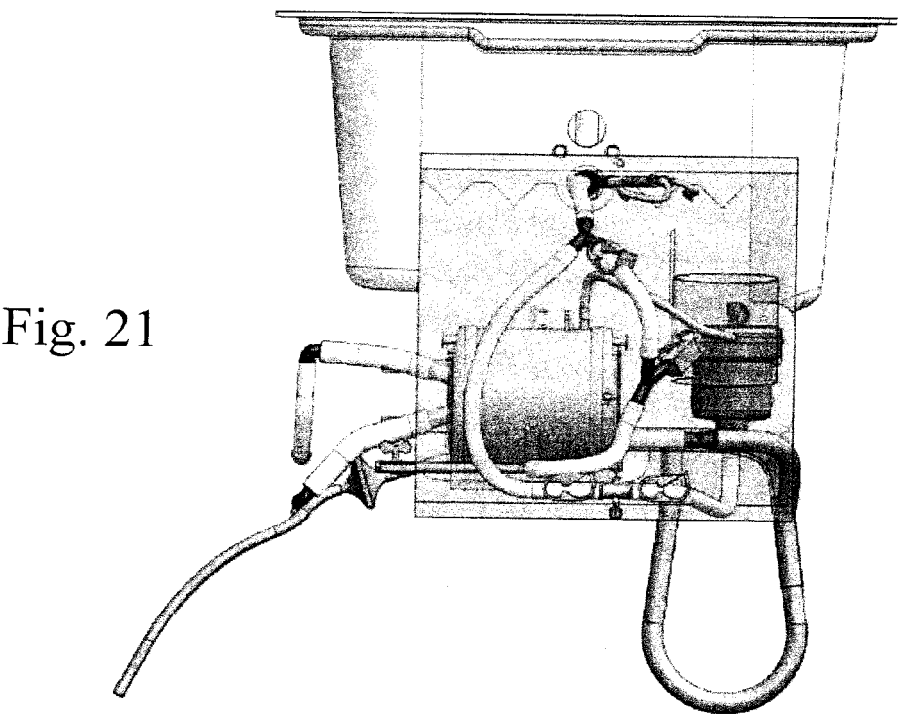
Figure 22:
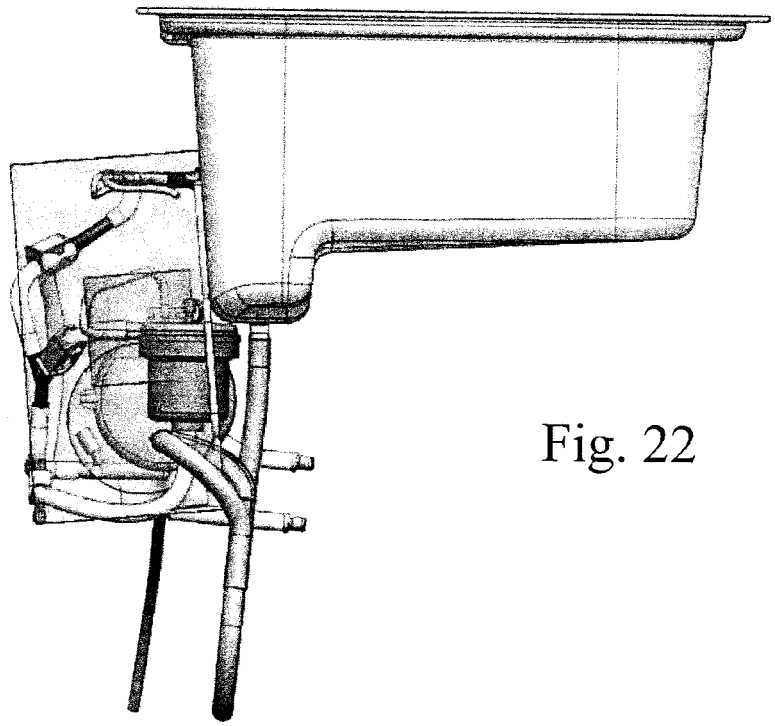

FIG. 18 shows another embodiment of the tube sets. In this embodiment, the pulmonary pressure sensors 116, 117 are arranged to the left, while the system pressure sensor 118 is arranged to the right.

The tube sets may be arranged in a cassette as shown in FIGS. 19 to 22. In principle, the tube sets are enclosed by a shell or cassette 121, which may be transparent or non-transparent. The tube portions, which interact with other components extend out of the shell or cassette 121 as shown in the different Figures.

Figure 23:
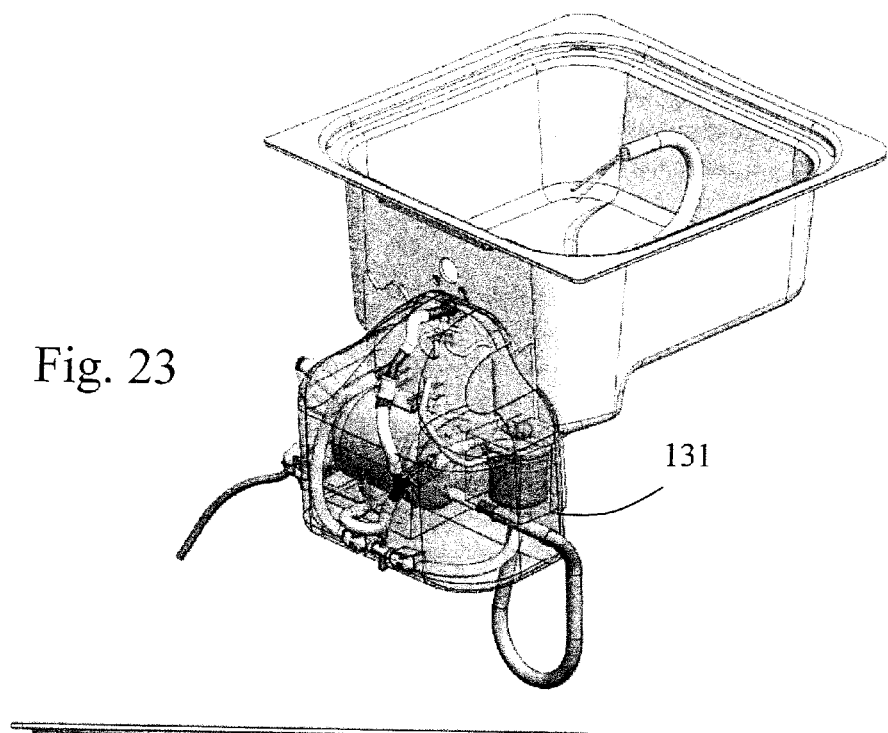
FIGS. 23 and 24 are perspective views similar to FIG. 19 of a second embodiment of the cassette.
Figure 24:
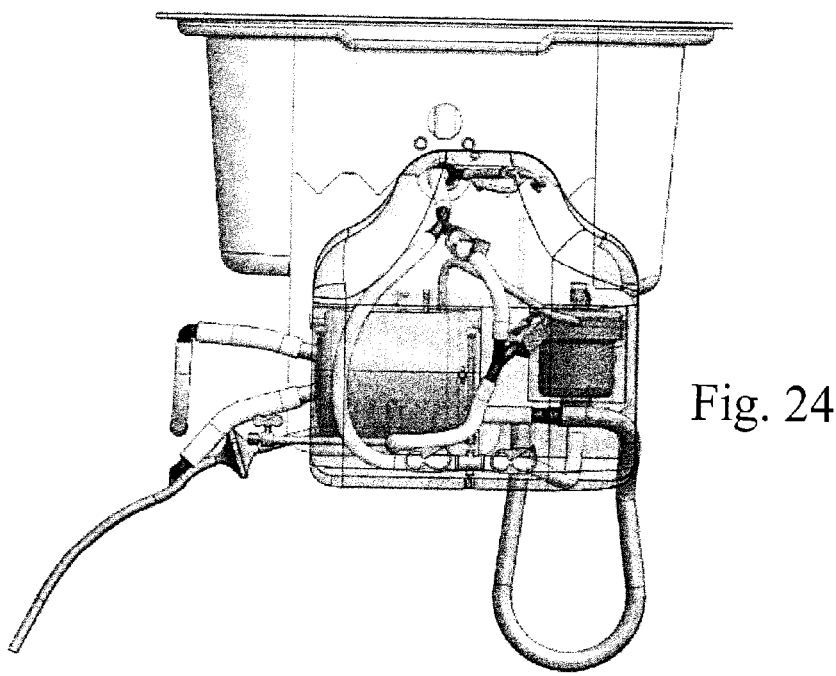

A second embodiment of the shell is shown in FIGS. 23 and 24. The shell or cassette 131 is more rounded compared to the first embodiment of the shell or cassette 121 shown in FIGS. 19 to 22.

Figure 25:
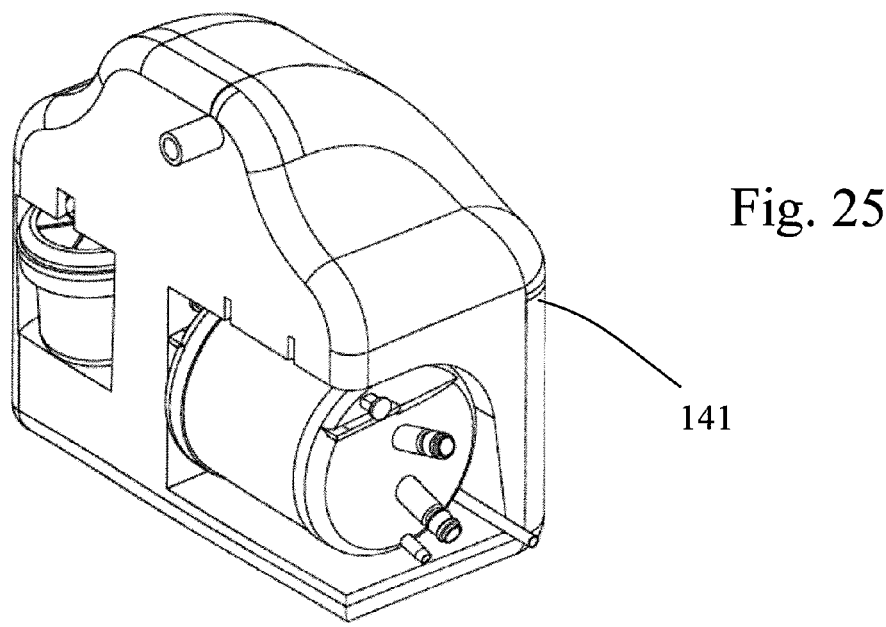
FIG. 25 is a perspective view from the backside of the cassette shown in FIG. 23.

A third embodiment of the shell or cassette 141 is shown in FIG. 25, wherein the oxygenator and the leucocyte filter are not included in the shell or cassette but may be inserted therein and connected in the circuit. In this manner, any oxygenator and leucocyte filter may be used. In addition, the leucocyte filter may be replaced during use, if it becomes depleated.

Figures 26, 27:
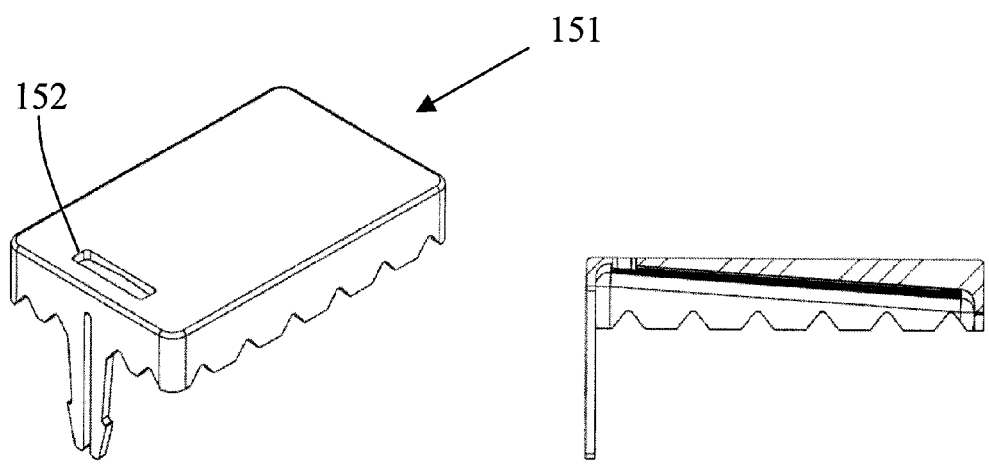
FIG. 26 is a perspective view of a plate included in the embodiment of FIG. 2.
FIG. 27 is a cross-sectional view of the plate of FIG. 26.

FIG. 27 is a perspective view of a plate 151, which is arranged above the outlet openings or nipples 82 and 85 in the bottom portion 11 in order to prevent air from being sucked into the openings and in order to prevent the formation of whirls. A cross-sectional view of the plate is shown in FIG. 27. The inside bottom surface is inclined as shown and ends in an elongated hole 152 for the escape of air. The same operation may be achieved by other means, which may be integrated in the bottom portion 11.

Figure 28:
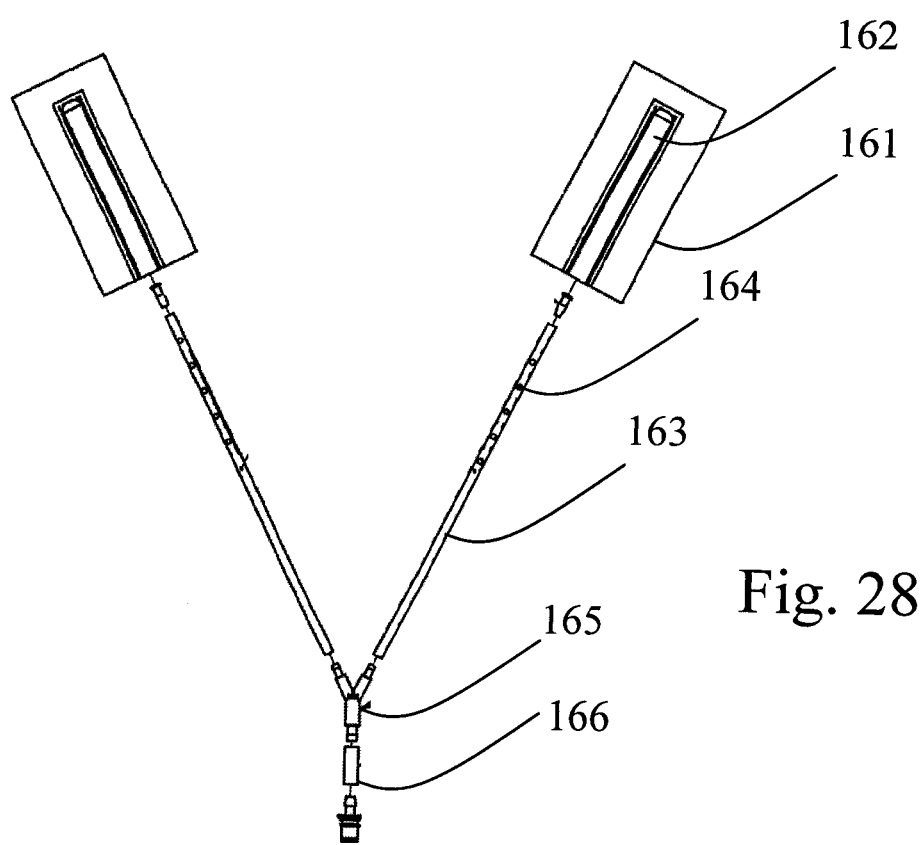
FIG. 28 is a plan view of a topical cooling unit for use in the embodiment of FIG. 2.

When it is desired to cool the lungs, several cloths may be arranged below and above the lungs. Then, several cooling cloths 161 are arranged there above. Two cooling cloths are shown in FIG. 28. Each cooling cloth comprises a pocket 162. A narrow tube 163 provided with several holes 164 is inserted in the pocket. The tube 163 is connected to a source of cold fluid via a Y-connector 165. The Y-connector is provided with a releasable coupling 166, which may be connected to the releasable coupling 37 arranged at the end of the bent tube 17. Another tube 163 may be connected to the second Y-connector 25 instead of tube 39 for providing cooling fluid to a central portion of the lungs.

The holes 164 may be formed by stamping out a semicircular or almost circular slit in the wall of the tube, thus forming a flap, which is attached to the tube by a web. When a fluid pressure exists inside the tube, the pressure exerts an opening force on the flap, which flexes outwards against the spring action of the web. Thus, the openings are opened and fluid passes out through the openings. By designing the slit and the size of the flap and the web, the out-flow of fluid through each opening may be controlled in order to obtain a uniform out-flow of fluid from each opening independent on the distance from the end. Because of the Bernoulli law, the static pressure in the openings closest to the end is larger than the static pressure at a larger distance from the end. By arranging the web stronger at the openings closest to the end and/or by arranging the flaps with smaller surface area at the openings closest to the end, the out-flow may be controlled.

Figure 29:
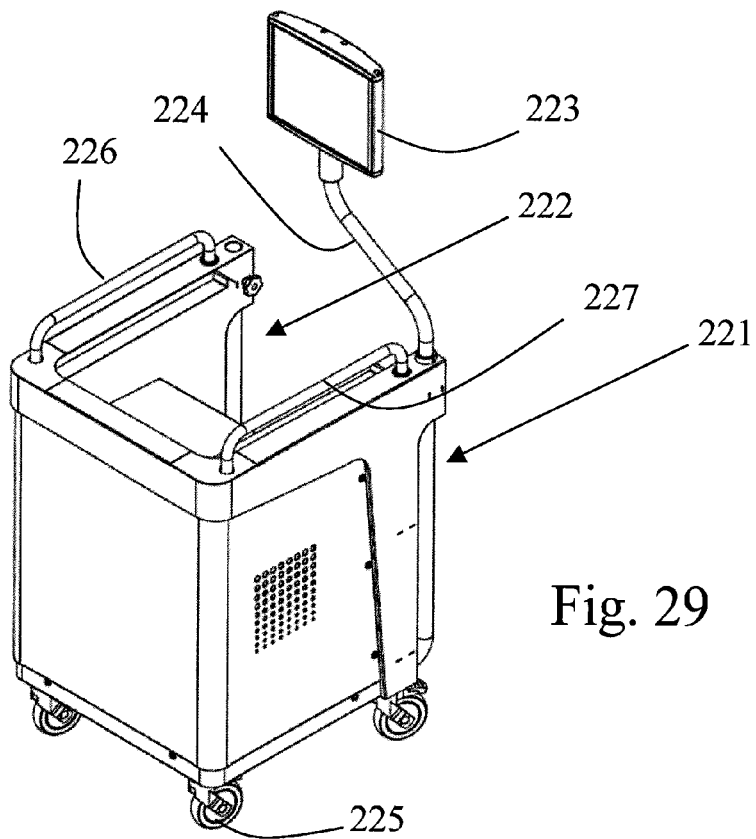
FIG. 29 is a perspective view of a supporting structure for the container according to FIG. 2.

The entire container assembly 11, 12, 13 including all tubing sets etc is arranged in a supporting structure 221 shown in FIG. 29. The supporting structure comprises a recess 222 shaped for receiving the container. In addition, the supporting structure comprises a display panel 223 pivotably arranged at a holder 224, which may be attached to the right as shown or to the left.

The supporting structure comprises four wheels 225 which are lockable. The lock may be arranged to lock the rotation of the wheels and/or the pivoting of the wheels. Two handle rods 226, 227 are arranged at the top surface as shown and may be used when transporting the structure 221.

Figure 30:
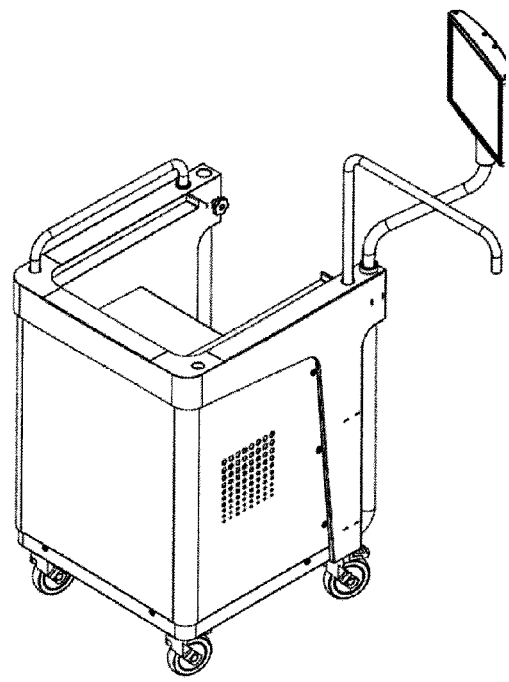
FIGS. 30 to 33 are perspective views similar to FIG. 29 with the supporting structure in different positions.
Figure 31:
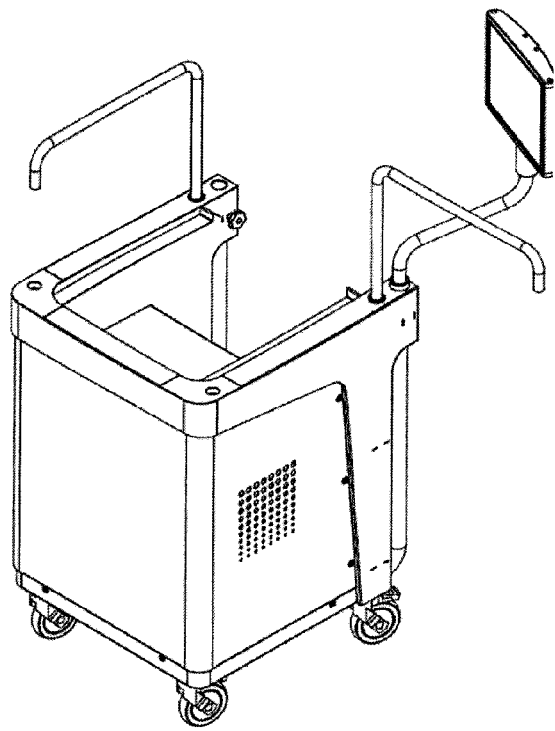
Figure 32:
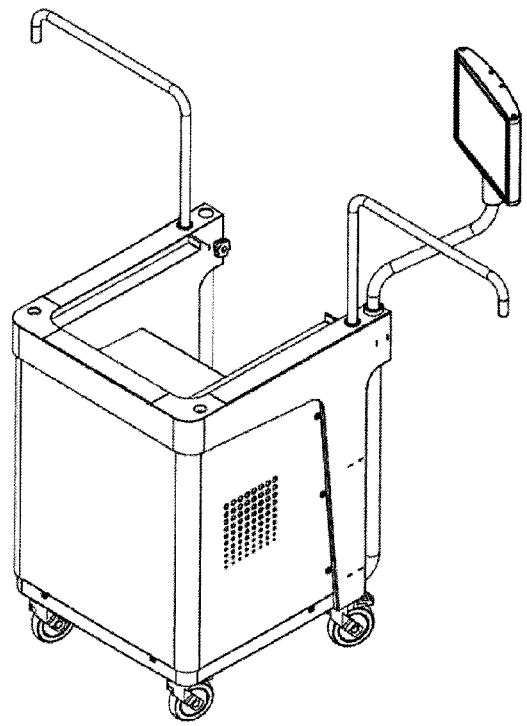

The handles 226 and 227 may be folded up and pivoted to the positions shown successively in FIGS. 30, 31 and 32. In the position shown in FIG. 32, the holders may support a sterile cloth 228 as shown in FIG. 33, which may be arranged in the container before use. The sterile cloth is unfolded and arranged at the holders 226, 227. In this way, the backside of the supporting structure comprising all connections and tubing sets is arranged at one side of the sterile cloth, which may be called a non-sterile side. At the front side, the surgeons may be situated. In this manner, there is formed a working place which is very flexible and wherein all persons which are active may perform their respective functions in a convenient manner.

The apparatus, container, tubing sets etc described above forms a set, which is well suited for evaluation, preservation and perfusion of lungs and other similar organs.

The container comprising the bottom portion 11, the insert portion 12 and the lid portion 13 and including the sterile clothing is sterilized in an assembled position. The tube sets or the shell structures 121, 131, 141 etc are also sterilized separately. For sterilization, Eto sterilization with ethylene oxide gas may be used. Alternative sterilization methods may be used, such as radiation sterilization, with alfa-, beta- or gamma-radiation may be used.

Figure 34:
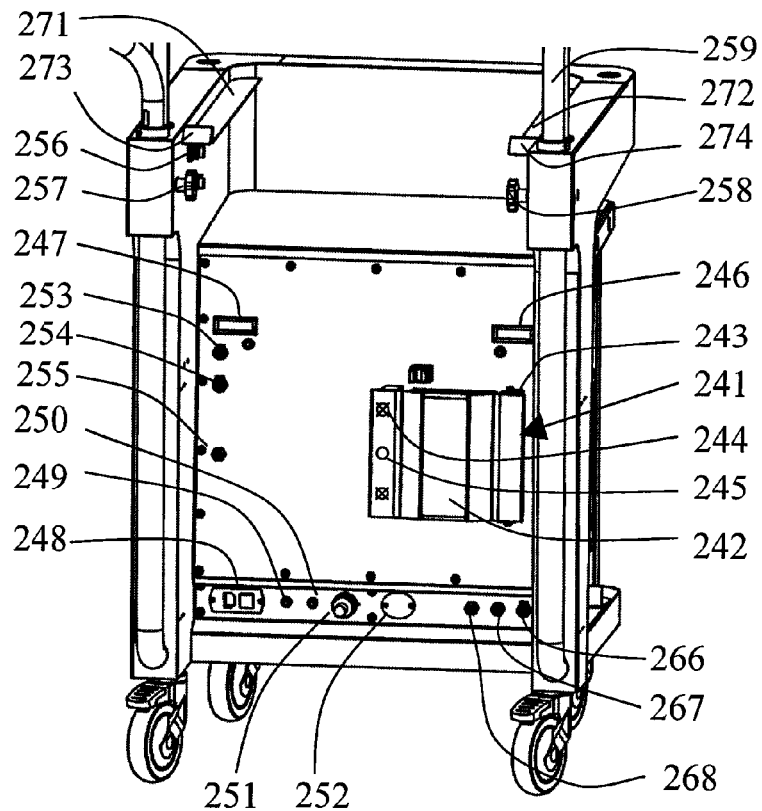
FIG. 34 is a perspective view of the backside of the supporting structure.
Figure 35:
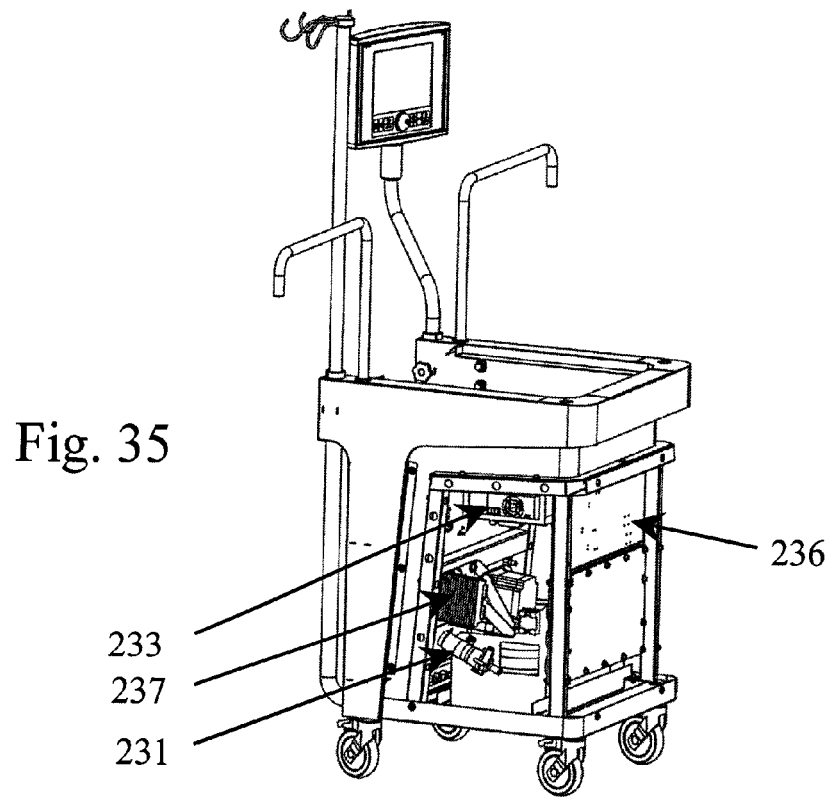
FIGS. 35 and 36 are perspective views of the supporting structure with panels removed for showing internal components.
Figure 36:
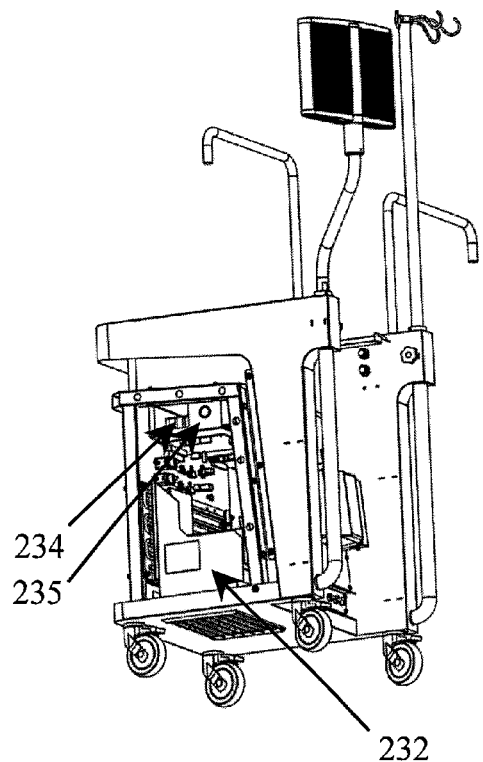

FIGS. 34 to 36 show the components included in the supporting structure 221. The backside of the structure 221 is called the non-sterile area. In this area all connections are arranged. FIG. 35 and FIG. 36 show the structure 221 with the front cover removed exposing the interior components, which includes a water pump 231, a heating and cooling unit 232, a power supply 233, a battery pack 234, a loudspeaker 235, a pneumatics unit 236, and a fluid motor control unit 237.

FIG. 34 shows the support structure from the backside. The backside comprises a fluid pump unit 241, which in the embodiment shown is a conventional peristaltic pump, but may alternatively be a centrifugal pump or membrane pump. The pump components are covered by a lid 242, which is pivotable around a shaft 243 at the right side as shown. The left portion of the lid comprises a magnetic lock 244, which keeps the lid in place during operation. An inductive sensor 245, such as a Hall element sensor, is arranged for indicating that the lid is closed. If the inductive sensor indicates that the lid is open, the operation of the pump cannot be initiated. The peristaltic pump is controlled by the fluid motor control unit 237 arranged inside the structure.

Two displays 246 and 247 for temperature are arranged at the backside as shown. Temperature sensors are connected via two connectors arranged below each display.

A power switch 248 is arranged for controlling the mains power supply to the supporting structure. Two automatic fuses 249, 250 are shown beside the power switch, one for control of a compressor and one for the control of a heater of the heating and cooling unit.

A connector 251 is arranged for connection of the display panel to the control circuits inside the supporting structure. The display panel may be arranged at the left side as shown in the figures or at the right side. The control circuits including a control computer and other electronics are arranged adjacent the power supply 233.

Beside the connector 251 there is a cover 252 enclosing a contact arrangement for a digital device, such as a USB memory stick or other memory device. The computer of the device may store data at such a memory device, which may be used for different purposes.

Nipples 253 and 254 for supply of cooling water to the oxygenator are further provided as well as a gas outlet connector nipple 255. Two pressure input connectors, one of which is shown at 256, are arranged at the left side, only one being shown in FIG. 34.

A locking screw 257 is arranged for locking the stand for the display panel in the desired adjusted position. A similar screw 258 is arranged at the other side for locking a stand 259 for priming bags as described below.

Figure 37:
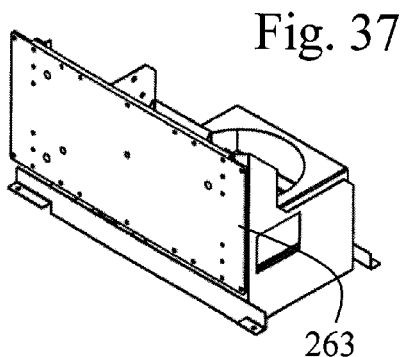
FIGS. 37 and 38 are perspective views of a heating and cooling unit of the supporting structure.
Figure 38:
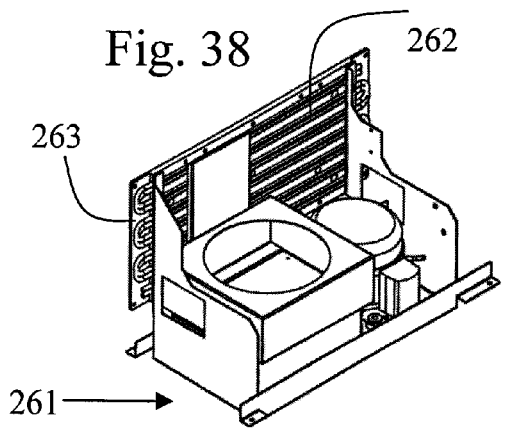

The heating and cooling unit 232 is shown in more detail in FIG. 37 and FIG. 38. The unit comprises a conventional cooling device 261, including a compressor and expansion device and all other required components. There are cooling tubes 262, for example of copper, which comprises the cooling medium arranged at a vertical plate 263.

Figure 39:
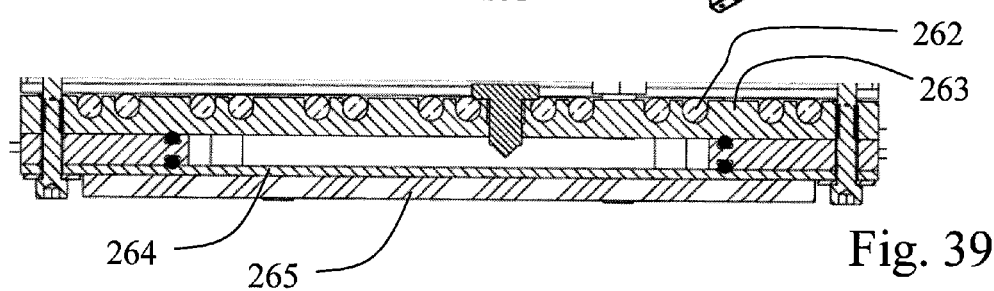
FIG. 39 is a horizontal section view of the unit shown in FIG. 37.

FIG. 39 shows the vertical plate 263 in a horizontal cross-sectional view. At the outside of the vertical plate and at a small distance from the vertical plate is arranged a second vertical plate 264 including an electric heating foil 265. Water is enclosed between the two vertical plates. The water is cooled by the copper tubes 262 and heated by the heating foil 265 in dependence of the desired temperature of the cooling water. The cooling water is circulated by the water pump 231, see FIG. 35 to the water outlet and inlet nipples 253 and 254, see FIG. 34. Cooling water is introduced into the system via a nipple 266, see FIG. 34, and removed from the system after use via the same nipple 266. In case there is an overpressure inside the cooling water system, there is arranged an overflow tube (not shown) having an opening at the height of the temperature sensors 246, 247 or slightly higher. A condensate water plate (not shown) is arranged below the cooling tubes 262 for collecting condensate water.

There may be different strategies for heating and cooling the water. If a low temperature is desired and if there is sufficient electric power available, the cooling device 261 may be operated continuously for providing sufficient cooling via the cooling tubes 262. If the temperature of the water becomes too low, the heating coils 265 are arranged for slightly heating the water to the right temperature, i.e. for fine adjustment of the temperature. If the device is operated on batteries, the cooling device may be controlled for providing no more than sufficient cooling, for example by intermittent operation. The heating foils 265 are used only when the water should be above room temperature, for example 37° C., which temperature may be used for evaluation.

Gas for ventilation of the lungs is normally taken from a gas supply, which is present at a hospital or other facility. Thus, there is a first gas inlet nipple 267 for oxygen and a second inlet gas nipple 268 for a mixture of nitrogen gas and carbon dioxide gas. The gas inlets open into the pneumatics unit 236 in which the proper proportioning and delivery of the gases takes place.

If gas supply is not available, there may be a separate gas supply device including gas sources, for example a separate supporting structure including the required components. In addition or alternatively, on-board gas supplies may be arranged. Other sources of gas may be connected to the nipples.

The proper mixing of gases may be performed outside the supporting structure. In this case, only a single nipple may be used for the gas supply. In other applications, there may be arranged on-board gas supplies for some gas components and external gas supplies for other gas components.

As appears from FIG. 34, the supporting structure comprises two horizontal shoulders 271 and 272 intended for supporting the container when inserted in the supporting structure. Each shoulder comprises a raised portion 273 and 274 at the outer end, which acts as a stop for the container when arranged at the shoulder so that the container cannot be easily removed or retracted. At the end of the shoulder opposite to the raised portion, a part of the supporting structure extends over the edge of the container preventing the container from being tilted upwards at this end. The shoulder provides a distance means, which results in that a distance is formed between the container and the supporting structure. This distance forms an insulating air layer, which helps in heat insulation of the container.

Figure 44:
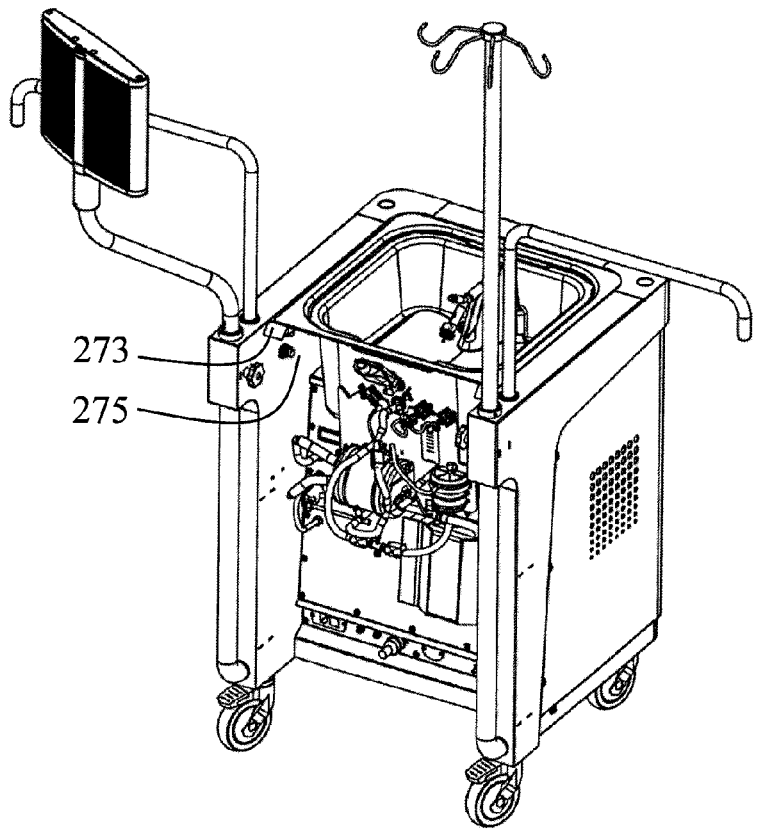
FIGS. 44 and 45 are a perspective view and an end view of the supporting structure provided with a container.
Figure 45:
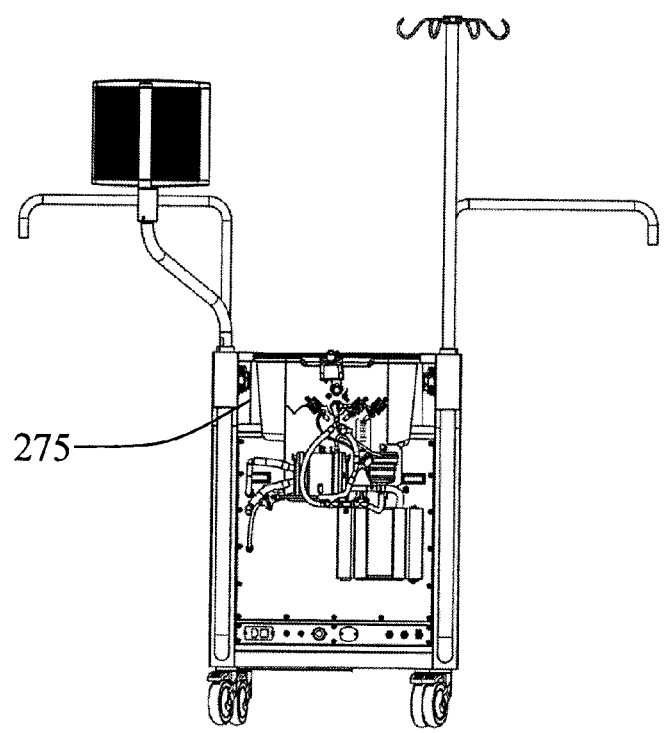

FIG. 44 shows the container in place in the supporting structure. The raised portion 273 interacts with the edge of the container for preventing unintentional removal thereof. At the same time, the shoulder 271 acts as a distance means to form a space 275 between the supporting structure and the container. The space surrounds the entire container and forms an insulating air layer, which heat insulates the container.

Figure 46:
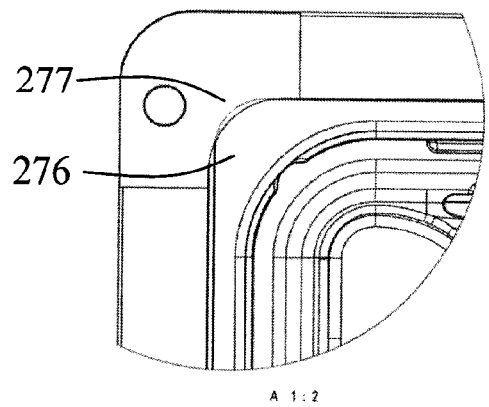
FIG. 46 is an enlarged view of a portion of the supporting structure and container shown in FIG. 44.
Figure 47:
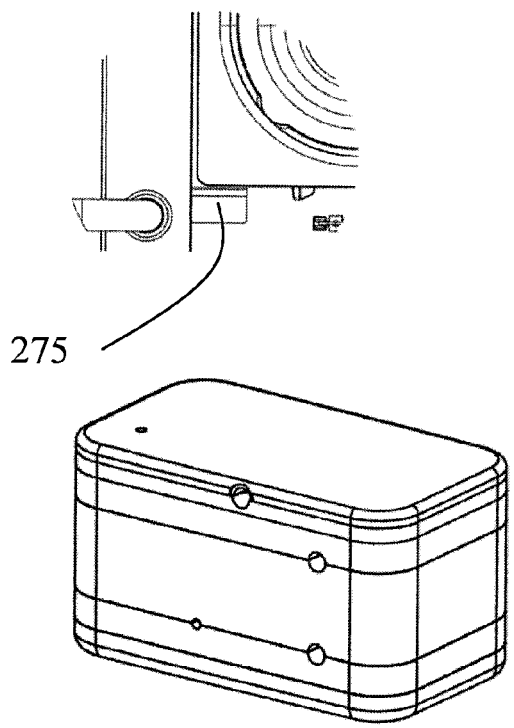
FIGS. 47 to 50 are perspective views of a further embodiment of the cassette.
Figure 48:
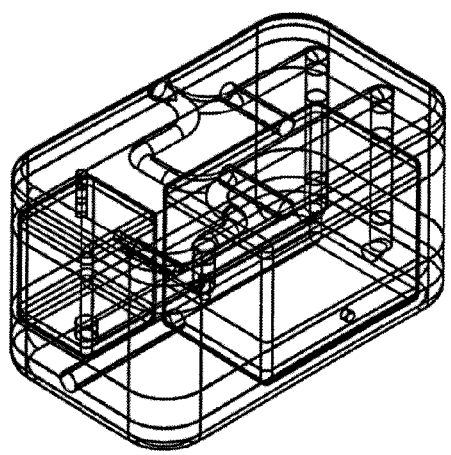

FIG. 46 shows in an enlarged scale the cooperation between the raised portion 273 and the container. In addition, FIG. 46 shows how the other corner 276 of the container extends below an edge portion 277 of the supporting structure, preventing the container from being raised vertically at this end.

Figure 40:
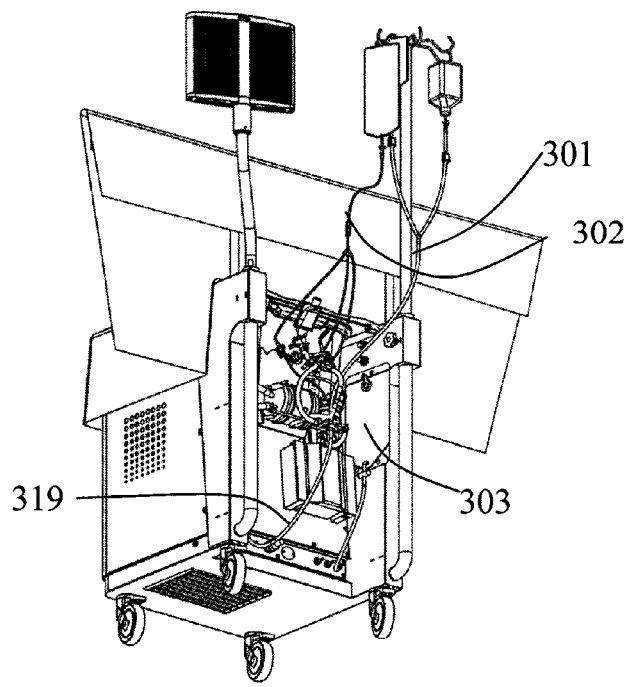
FIGS. 40 and 41 are perspective views of the supporting structure including a priming set.
Figure 41:
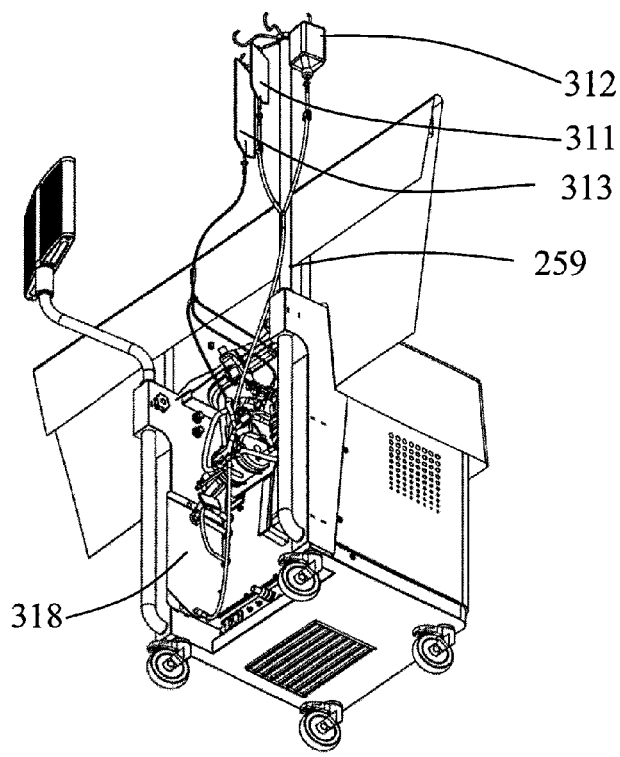

FIG. 40 and FIG. 41 shows the supporting structure during priming of the container and the tube sets. The supporting structure is arranged as described above in connection with FIG. 33 with the sterile cloth.

Figure 42:
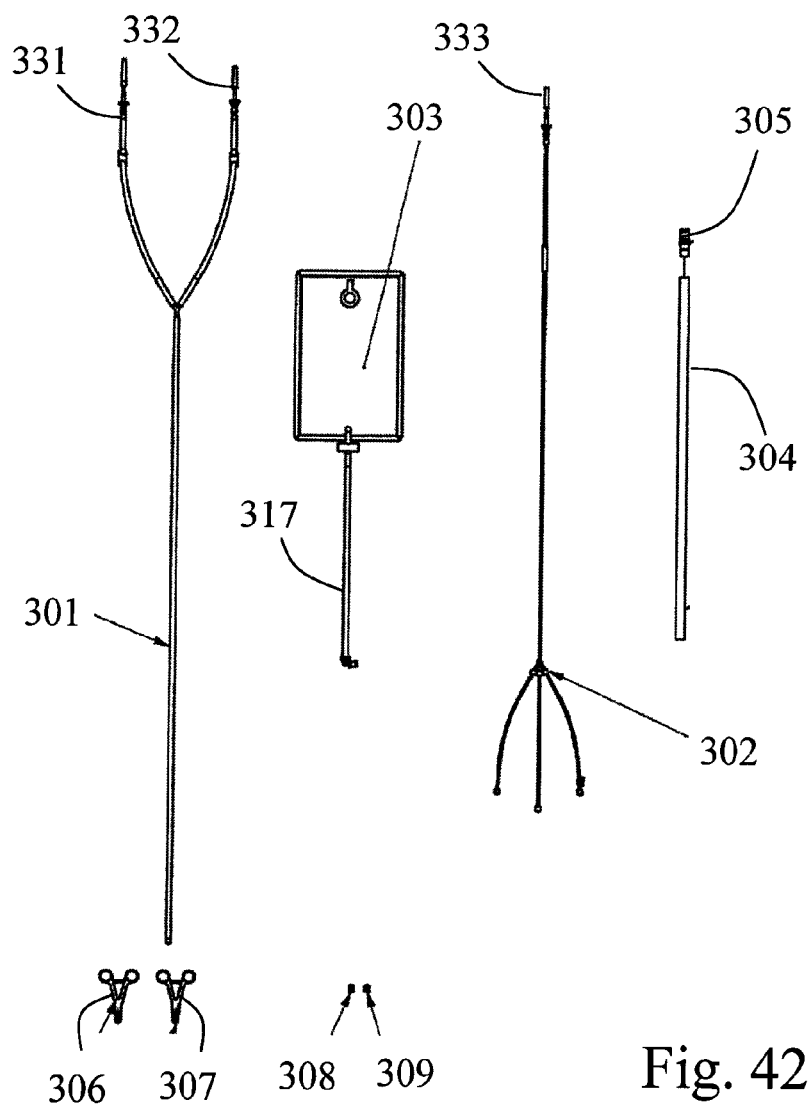
FIG. 42 is a schematic view of the priming set.

The priming tube set comprises, as shown in FIG. 42, an infusion priming tube 301, a pressure sensor flush tube set 302 and a water bag 303 with a water bag tube 317. In addition, there is a discharge tube 304 and a releasable coupling 305. Furthermore, there are two hemostatic forceps or squeezing devices 306, 307 for arranging the sterile cloth in a convenient position and two caps 308, 309.

In addition as shown in FIG. 41, an erythrocyte bag 311 and a infusion fluid bottle 312 are arranged at the stand 259 and comprising fluid to be used in the vascular system of the organ. The infusion fluid is an evaluation or preservation fluid, such as Steen Solution. A third bag 313 is arranged comprising sterile water or sterile saline solution. The bags are arranged at the stand 259 as shown in FIG. 41.

A waste bag 318 and a waste bag tube 319 are arranged at the bottom side of the supporting structure as shown in FIG. 41. The infusion priming tube 301 comprises two spikes 331 and 332 at the bifurcated end. The spikes are inserted in the erythrocyte bag 311 and the bottle 312, as shown in FIG. 40. The spike 332 inserted in the bottle 312 should be a so-called vented spike, since the bottle may be non-flexible.

The pressure sensor flush tube set 302 comprises a spike 333 at the single end, which is inserted in the third bag 313. The other three ends of the pressure sensor flush tube set 302 are connected to three pressure sensors 111, 112, 113, which are shown for example in FIG. 17. The pressure sensors comprise three nipples 314, 315, 316 to which the ends of the pressure sensor flush tube set 302 are connected. When an area of the pressure sensor is squeezed, the fluid is free to flow through the pressure sensor under the influence of gravity and out through a tube connected to the other end of the pressure sensor. In this way, the pressure sensors are primed and all air is expelled from the pressure sensors and associated tubes. When the priming is finalized, the pressure sensor flush tube set 302 is removed.

The free ends of the infusion priming tube 301 and the waste bag tube 319 are connected to two nipples 337, 338 of the leukocyte tube set shown in FIG. 12 and FIG. 14. The two portions having spikes inserted in the bags 311, 312 comprises clamps, which are operated so that fluid enters the lines down to the connection point. Then, the clamp of the erythrocyte bag is closed and the clamp of the fluid bottle is left open.

Figure 43:
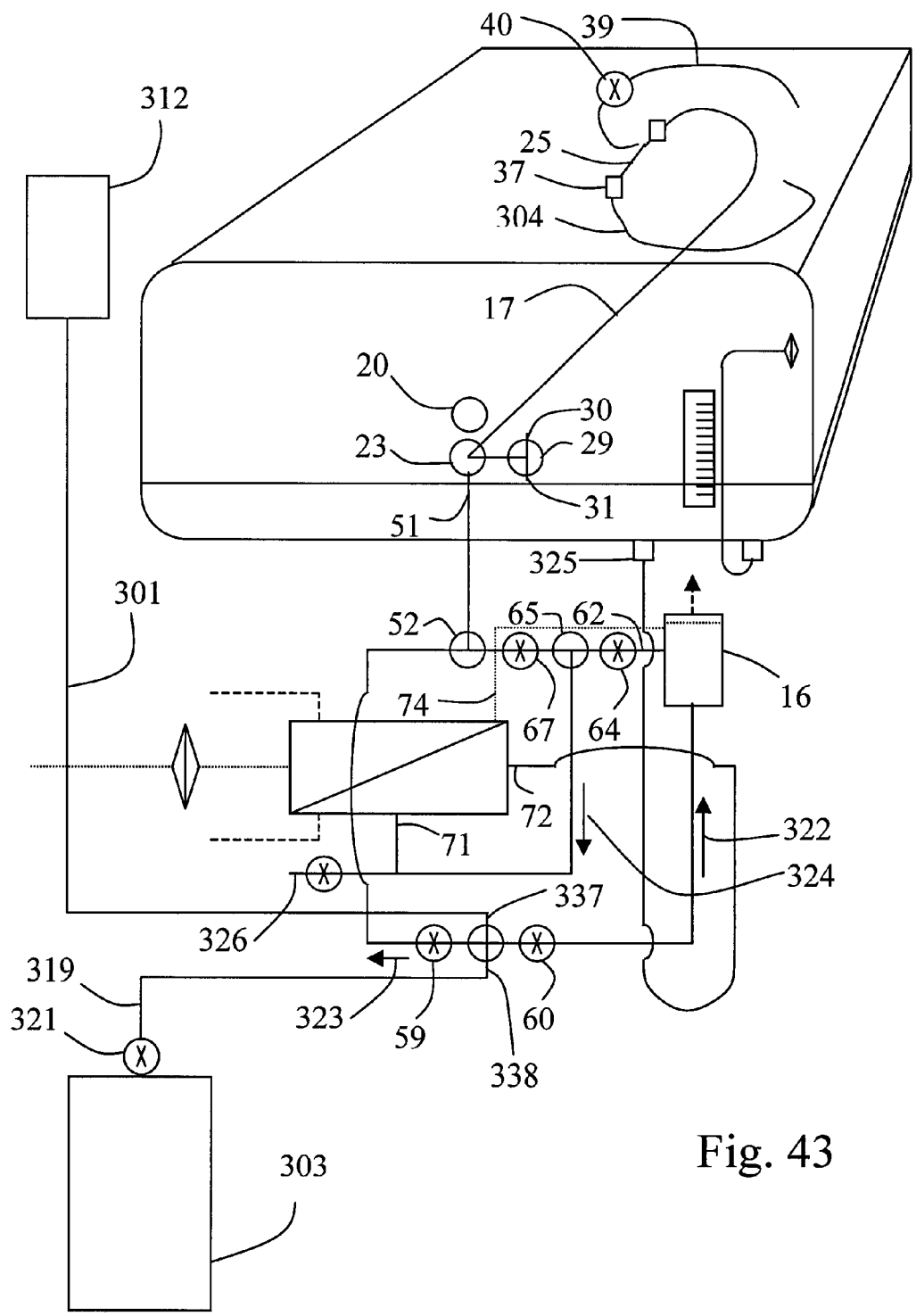
FIG. 43 is a schematic view showing the tube sets during priming.

The operation of the priming will now be explained with reference to FIG. 43, which is a schematic view similar to FIG. 14. The fluid in the infusion priming bottle 312 will enter the leukocyte filter tube set at inlet 337. Since a clamp 321 of the waste bag tube 319 is closed, no fluid will pass down to the water bag 303 via nipple 338.

In the leukocyte filter tube set, the clamp 64 is closed while the other clamps 59, 60 and 67 are open. Thus the infusion fluid will pass according to arrow 322 and fill the leukocyte filter while displacing the air in the tube set and leukocyte filter until the filter is full of fluid.

Simultaneously, the infusion fluid passes according to arrow 323 and up to the Y-connector 65 and further according to arrow 324 via Y-connector 52, clamp 67 and Y-connector 65 to the bottom of the oxygenator at outlet connector 71. The infusion fluid flows in a direction opposite to the normal through the oxygenator and displaces air inside the oxygenator via inlet 72 and also possibly via vent tube 74. Since the pump segment is not inserted in the pump, flow can take place via the inlet connector 72 and via the pump segment to the bottom of the container, until all the fluid has entered the container.

The clamp 64 may now be opened to displace air in this portion of the tube set. The clamp 60 is closed.

The tube 304 has been connected to the releasable coupling 37 and opens freely in the bottom of the container. The pump segment is introduced into the peristaltic pump and the pump starts to pump fluid in the normal direction at a slow speed. Fluid and possible air left in the system are displaced through the oxygenator, the leukocyte filter and to the bent tube 17 and further to the releasable coupling 37 and further via tube 304 to the bottom of the container, inside the insert portion. There are several holes for passing the fluid down below the insert portion to the bottom portion.

The pump segment may be calibrated so that the pump has a correct occlusion. The occlusion is controlled by a control device in the pump unit, which influences upon the rollers of the pump to press the rollers with a suitable force against the pump segment. The calibration takes place by arranging the pump segment in the peristaltic pump with the rollers in a non-engaged position, whereupon the rollers are engaged until the system pressure meter indicates that a sufficient system pressure has been obtained. In this manner, a suitable roller engagement can be obtained automatically.

As described above, all portions of the tube sets and the other components of the disposable set is filled with infusion fluid and the surplus of the infusion fluid is enclosed at the bottom of the container. Finally, the connection to the erythrocyte bag 312 is opened and the erythrocytes are introduced into the tube set.

The fluid with erythrocytes is allowed to circulate for a while until it has obtained a stable temperature and stable gas concentrations as desired. Additional agents may be added, such as medicinal agents and other components, such as hormones, nutrition, etc.

Finally, the pump is stopped and the lungs are introduced and connected to the system as described above.

During the operation, the priming set is left in position, in case further fluid should be required.

When the system should be emptied from fluid, the clamp 321 is opened and almost all fluid is removed by gravity to the bag via nipple 338. The air outlet of the leukocyte filter should be closed in order not to disrupt the complete emptying of the oxygenator and the pump segment, which takes place at a slight under pressure.

Finally, the priming components are removed and the two caps 308, 309 may be arranged over the nipples 337, 338 to prevent fluid from being discharged there from.

Hereinabove, one manner of priming the system has been described. Other manners may be used, for example by introducing infusion fluid to infusion inlet 337 and at the same time to a sample port 326 at the outlet 71 of the oxygenator. The emptying of the tube system may also alternatively or additionally use the sample port 326.

The heating and cooling unit is filled with water from the water bag 303 arranged at the side of the supporting structure as shown in FIG. 39. The water bag 303 is connected to the water inlet nipple 266 shown in FIG. 34.

As appears from FIG. 39 and FIG. 40, the supporting structure comprises panels surrounding the interior components. The panels may be provided with openings as shown so that air may be ventilated to the interior of the structure.

Figure 49:
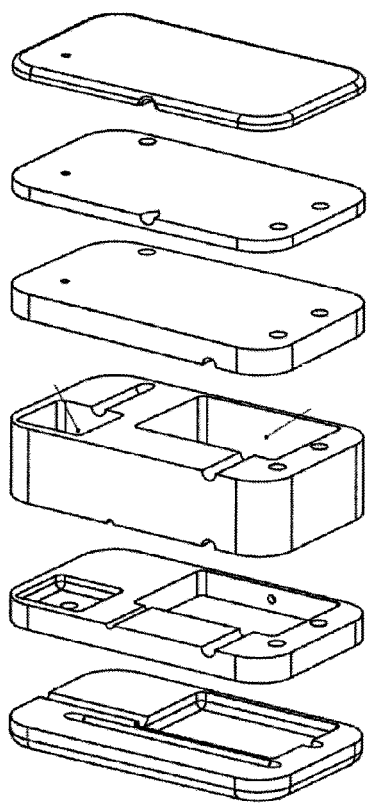
Figure 50:
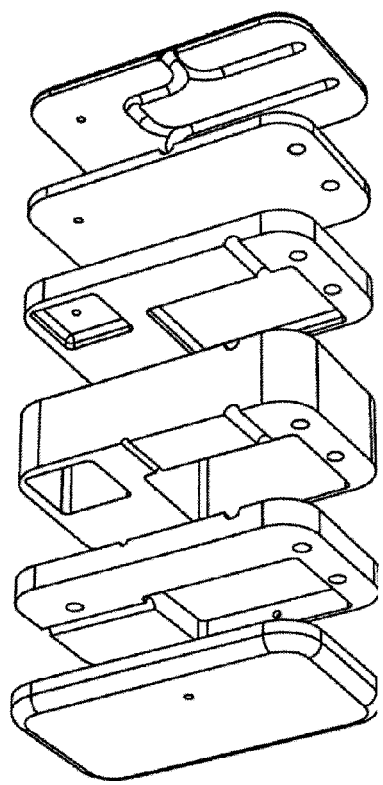

FIGS. 47 to 50 shows another design of the cassette including the oxygenator and leukocyte tube sets. As shown in FIGS. 49 and 50, the cassette 351 comprises 6 plates comprising recesses in both the upper and lower surfaces. When the plates are connected together, the desired tube sets are formed.

In the claims, the term "comprises/comprising" does not exclude the presence of other elements or steps. Furthermore, although individually listed, a plurality of means, elements or method steps may be implemented by e.g. a single unit. Additionally, although individual features may be included in different claims or embodiments, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

Although the present invention has been described above with reference to specific embodiment and experiments, it is not intended to be limited to the specific form set forth herein. Rather, the invention is limited only by the accompanying claims and, other embodiments than those specified above are equally possible within the scope of these appended claims.

The invention claimed is:

1. An apparatus intended for evaluation, preservation and/or perfusion of a lung, comprising:
   a container having a bottom portion, an insert portion and a lid portion;
   a pulmonary artery tube intended to be connected to a lung pulmonary artery:
   a trachea tube intended to be connected to a trachea of the lungs;
   a bent tube for connection of the pulmonary artery tube to a circuit for providing a fluid to the pulmonary artery, said circuit comprising a pump and an oxygenator and an optional leukocyte-filter, said bent tube being bent over about 180 degrees inside said container;
   a vortex preventing plate; and
   a holder for connecting the trachea tube to a source of ventilation, wherein said trachea tube and said bent tube are arranged to pass through one and the same side wall of the container.

2. The apparatus according to claim 1, further comprising a tube set arranged outside of the container for enclosing fluid to be circulated through the organ, said tube set being arranged as a cassette.

3. The apparatus according to claim 1, further comprising an oxygenator tube set and optionally a leukocyte-filter tube set.

4. The apparatus according claim 1, further comprising a topical cooling cloth provided with a pocket and a narrow tube extending into said pocket for providing cold fluid to said pocket and to said cloth.

5. The apparatus according to claim 1, further comprising pressure sensor tubes and temperature measurement sensors, having lead-through arrangements passing through one and the same side wall of the container as said trachea tube and said bent tube.

6. A supporting structure intended for evaluation, preservation and/or perfusion of a lung, said supporting structure comprising:
- a container having a bottom portion, an insert portion and a lid portion;
- a pulmonary artery tube intended to be connected to a lung pulmonary artery:
- a trachea tube intended to be connected to a trachea of the lungs;
- a bent tube for connection of the pulmonary artery tube to a circuit for providing a fluid to the pulmonary artery, said circuit comprising a pump and an oxygenator and an optional leukocyte-filter, said bent tube being bent over about 180 degrees inside said container;
- a vortex preventing plate; and
- a holder for connecting the trachea tube to a source of ventilation,
- wherein said trachea tube and said bent tube are arranged to pass through one and the same side wall of the container;
- whereby said supporting structure comprises two horizontal shoulders intended for supporting the container when inserted in the supporting structure, said shoulders providing a distance means, whereby a distance is formed between the container and the supporting structure forming an insulating air layer for heat insulation of the container.

7. The supporting structure according to claim 6, further comprising a priming tube set.

8. The supporting structure according to claim 6, further comprising at least one of the following components: a water pump, a heating and cooling unit, a power supply, a battery pack, a loudspeaker, a pneumatics unit and a fluid pump unit.

* * * * *